(12) United States Patent
Ruike et al.

(10) Patent No.: US 11,827,717 B2
(45) Date of Patent: Nov. 28, 2023

(54) ANTI-MASP-1 ANTIBODIES AND METHODS OF USE

(71) Applicant: Chugai Seiyaku Kabushiki Kaisha, Tokyo (JP)

(72) Inventors: Yoshinao Ruike, Kanagawa (JP); Taku Fukuzawa, Singapore (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 289 days.

(21) Appl. No.: 16/500,162

(22) PCT Filed: Apr. 2, 2018

(86) PCT No.: PCT/JP2018/014046
§ 371 (c)(1),
(2) Date: Oct. 2, 2019

(87) PCT Pub. No.: WO2018/186322
PCT Pub. Date: Oct. 11, 2018

(65) Prior Publication Data
US 2021/0115154 A1   Apr. 22, 2021

(30) Foreign Application Priority Data
Apr. 3, 2017   (JP) .................................. 2017-073428

(51) Int. Cl.
| | |
|---|---|
| *C07K 16/40* | (2006.01) |
| *A61P 7/00* | (2006.01) |
| *A61K 39/00* | (2006.01) |

(52) U.S. Cl.
CPC ............... *C07K 16/40* (2013.01); *A61P 7/00* (2018.01); *A61K 2039/505* (2013.01); *C07K 2317/33* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2013/0344073 A1 * 12/2013 Schwaeble ............. C07K 16/18
424/136.1

FOREIGN PATENT DOCUMENTS

| WO | WO 2004050907 A2 | 6/2004 |
| WO | WO 2013180834 A2 | 12/2013 |
| WO | WO 2013192240 A2 | 12/2013 |
| WO | WO 2014144542 A2 | 9/2014 |

OTHER PUBLICATIONS

Schroeder et al. (J Allergy Clin Immunol 2010, 125:S41-S52).*
Lloyd et al. Protein Engineering, Design & Selection 2009, 22:159-168.*
Product Data Sheet, Anti-MASP-1 antibody ab65891 (2009).
Takahashi, K., et al., "Mannose-binding lectin and its associated proteases (MASPs) mediate coagulation and its deficiency is a risk factor in developing complications from infection, including disseminated intravascular coagulation," Immunobiology, 216:96-102 (2011).
Thiel, S., et al., "Mannan-binding lectin (MBL)-associated serine protease-1 (MASP-1), a serine protease associated with humoral pattern-recognition molecules: normal and acute-phase levels in serum and stoichiometry of lectin pathway components," Clin Exp Immunol., 169:38-48 (2012).
Atik, T., et al., "Novel MASP1 mutations are associated with an expanded phenotype in 3MC1 syndrome," Orphanet Journal of Rare Diseases, 10:128 (2015), 12 pages.
Castellano, G., et al., "Therapeutic Targeting of Classical and Lectin Pathways of Complement Protects from Ischemia-Reperfusion-Induced Renal Damage," Am J Pathol., 176(4):1648-1659 (2010).
Dobo, J., et al., "The emerging roles of mannose-binding lectin-associated serine proteases (MASPs) in the lectin pathway of complement and beyond," Immunol Rev., 274:98-111 (2016).
Garred, P., et al., "A journey through the lectin pathway of complement-MBL and beyond," Immunol Rev., 274:74-97 (2016).
Holers, V. M., "Complement and its Receptors: New Insights into Human Disease," Annu Rev Immunol., 32:433-459 (2014).
La Bonte, L. R., et al., "Mannose-Binding Lectin-Associated Serine Protease-1 is a Significant Contributor to Coagulation in a Murine Model of Occlusive Thrombosis," J Immunol., 188:885-891 (2012).
Liu, L.-L., et al., "Glomerular mannose-binding lectin deposition is a useful prognostic predictor in immunoglobulin A nephropathy," Clin Exp Immunol., 174:152-160 (2013).

* cited by examiner

*Primary Examiner* — Sharon X Wen
(74) *Attorney, Agent, or Firm* — Nixon & Vanderhye P.C.

(57) ABSTRACT

The present invention provides anti-MASP-1 (mannan-binding lectin (MBL)-associated serine protease 1) antibodies and methods of using the same. In some embodiments, an anti-MASP-1 antibody of the invention binds to MASP-1 but does not bind to MASP-3. The invention also provides nucleic acids comprising a nucleotide sequence encoding an anti-MASP-1 antibody of the present invention. The invention further provides pharmaceutical compositions comprising an anti-MASP-1 antibody of the present invention and a pharmaceutically acceptable carrier.

16 Claims, 4 Drawing Sheets
Specification includes a Sequence Listing.

Figure 1

```
SEQ ID NO: 7    1   IFNGRPAQKGTTPWIAML-----SHL-NGQPFCGGSLLGSSWIVTAAHCL    44
SEQ ID NO: 11   1   IIGGRNAEPGLFPWQALIVVEDTSRVPNDKWFGSGALLSASWILTAAHVL    50

SEQ ID NO: 7   45   HQSLDPEDPTLRDSDLL--SPSDFKIILGKHWRLRSDENEQHLGVKHTTL    92
SEQ ID NO: 11  51   RSQ-------RRDTTVIPVSKEHVTVYLGLH-DVRDKSGAVNSSAARVVL    92

SEQ ID NO: 7   93   HPQYDPNTFENDVALVELLESPVLNAFVMPICLP----EGPQQEGAMVIV   138
SEQ ID NO: 11  93   HPDFNIQNYNHDIALVQLQEPVPLGPHVMPVCLPRLEPEGPAPHMLGLVA   142

SEQ ID NO: 7  139   SGWG-----------KQFLQRFPETLMEIEIPIVDHSTCQKAYAPLKKK-   176
SEQ ID NO: 11 143   GWGISNPNVTVDEIISSGTRTLSDVLQYVKLPVVPHAECKTSYESRSGNY   192

SEQ ID NO: 7  177   -VTRDMICAGEKEGGKDACAGDSGGPMVTLNRERGQWYLVGTVSWG--DD   223
SEQ ID NO: 11 193   SVTENMFCAGYYEGGKDTCLGDSGGAFVIFDDLSQRWVVQGLVSWGGPEE   242

SEQ ID NO: 7  224   CGKKDRYGVYSYIHHNKDWIQRVTG---------VRN              251
SEQ ID NO: 11 243   CGSKQVYGVYTKVSNYVDWVWEQMGLPQSVVEPQVER              279
```

Figure 2

```
SEQ ID NO: 7    1   IFNGRPAQKGTTPWIAMLSHLNGQPFCGGSLLGSSWIVTAAHCLHQSLDP    50
SEQ ID NO: 8    1   IFNGRPAQQGTTPWIAMLSHLNGQPFCGGSLLGSSWIVTAAHCLHQSLDP    50
SEQ ID NO: 9    1   IFNGRPAQKGTMPWIAMLSHLNGQPFCGGSLLGSNWVLTAAHCLHQSLDP    50

SEQ ID NO: 7   51   EDPTLRDSDLLSPSDFKIILGKHWRLRSDENEQHLGVKHTTLHPQYDPNT   100
SEQ ID NO: 8   51   EDPTLRNSDLLSPSDFKIILGKHWRLQSDENEQHLGVKHITLHPQYDPST   100
SEQ ID NO: 9   51   EDPTLHSSYLLSPSDFKIIMGKHWRRSDEDEQHLHVKRTTLHPLYNPST   100

SEQ ID NO: 7  101   FENDVALVELLESPVLNAFVMPICLPEGPQQEGAMVIVSGWGKQFLQRFP   150
SEQ ID NO: 8  101   FENDVALVELLESPVLNAFVMPICLPEGPQQEGAMVIVSGWGKQFLQRFP   150
SEQ ID NO: 9  101   FENDLGLVELSESPRLNDFVMPVCLPEQPSTEGTMVIVSGWGKQFLQRFP   150

SEQ ID NO: 7  151   ETLMEIEIPIVDHSTCQKAYAPLKKKVTRDMICAGEKEGGKDACAGDSGG   200
SEQ ID NO: 8  151   ETLMEIEIPIVDHDTCQKAYAPLKKKVTRDMICAGEKEGGKDACAGDSGG   200
SEQ ID NO: 9  151   ENLMEIEIPIVNSDTCQEAYTPLKKKVTKDMICAGEKEGGKDACAGDSGG   200

SEQ ID NO: 7  201   PMVTLNRERGQWYLVGTVSWGDDCGKKDRYGVYSYIHHNKDWIQRVTGVR   250
SEQ ID NO: 8  201   PMVTLNRERGQWYLVGTVSWGDDCGKKDRYGVYSYIHHNKDWIQRVTRLR   250
SEQ ID NO: 9  201   PMVTKDAERDQWYLVGVVSWGEDCGKKDRYGVYSYIYPNKDWIQRITGVR   250

SEQ ID NO: 7  251   N                                                   251
SEQ ID NO: 8  251   N                                                   251
SEQ ID NO: 9  251   N                                                   251
```

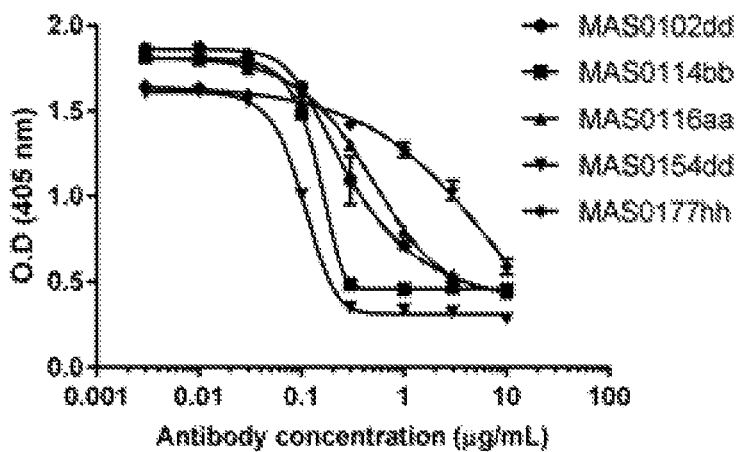
Figure 3A Human
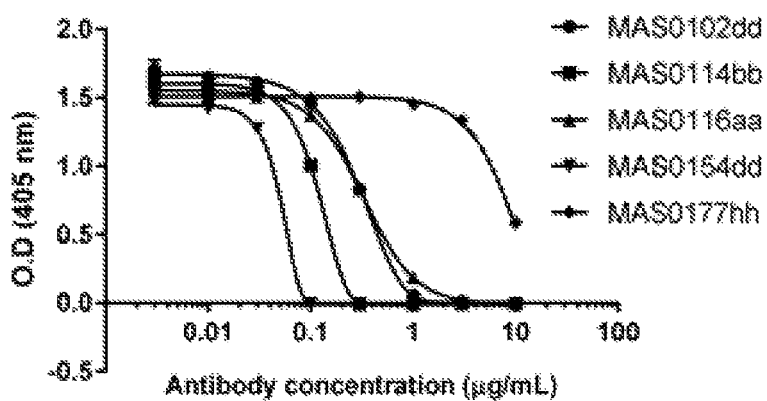
Figure 3B Cynomolgus monkey
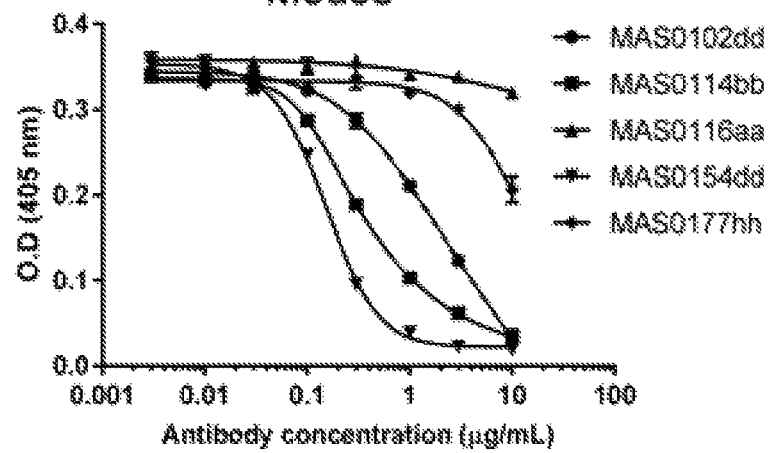
Figure 3C Mouse

SEQUENCE LISTING

```
<160> NUMBER OF SEQ ID NOS: 70

<210> SEQ ID NO 1
<211> LENGTH: 699
<212> TYPE: PRT
<213> ORGANISM: Homo sapiens

<400> SEQUENCE: 1

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300
```

-continued

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
            325                 330                 335

Lys Asp Asn Val Glu Met Asp Thr Phe Gln Ile Glu Cys Leu Lys Asp
        340                 345                 350

Gly Thr Trp Ser Asn Lys Ile Pro Thr Cys Lys Ile Val Asp Cys Arg
    355                 360                 365

Ala Pro Gly Glu Leu Glu His Gly Leu Ile Thr Phe Ser Thr Arg Asn
370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
            405                 410                 415

Gln Gly Val Trp Met Asn Lys Val Leu Gly Arg Ser Leu Pro Thr Cys
        420                 425                 430

Leu Pro Val Cys Gly Leu Pro Lys Phe Ser Arg Lys Leu Met Ala Arg
    435                 440                 445

Ile Phe Asn Gly Arg Pro Ala Gln Lys Gly Thr Thr Pro Trp Ile Ala
450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
            485                 490                 495

Asp Pro Glu Asp Pro Thr Leu Arg Asp Ser Asp Leu Leu Ser Pro Ser
        500                 505                 510

Asp Phe Lys Ile Ile Leu Gly Lys His Trp Arg Leu Arg Ser Asp Glu
    515                 520                 525

Asn Glu Gln His Leu Gly Val Lys His Thr Thr Leu His Pro Gln Tyr
530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
            565                 570                 575

Pro Gln Gln Glu Gly Ala Met Val Ile Val Ser Gly Trp Gly Lys Gln
        580                 585                 590

Phe Leu Gln Arg Phe Pro Glu Thr Leu Met Glu Ile Glu Ile Pro Ile
    595                 600                 605

Val Asp His Ser Thr Cys Gln Lys Ala Tyr Ala Pro Leu Lys Lys Lys
610                 615                 620

Val Thr Arg Asp Met Ile Cys Ala Gly Glu Lys Glu Gly Gly Lys Asp
625                 630                 635                 640

Ala Cys Ala Gly Asp Ser Gly Gly Pro Met Val Thr Leu Asn Arg Glu
            645                 650                 655

Arg Gly Gln Trp Tyr Leu Val Gly Thr Val Ser Trp Gly Asp Asp Cys
        660                 665                 670

Gly Lys Lys Asp Arg Tyr Gly Val Tyr Ser Tyr Ile His His Asn Lys
    675                 680                 685

Asp Trp Ile Gln Arg Val Thr Gly Val Arg Asn
690                 695

<210> SEQ ID NO 2
<211> LENGTH: 2097
<212> TYPE: DNA

<213> ORGANISM: Homo sapiens

<400> SEQUENCE: 2

| | | | | | | |
|---|---|---|---|---|---|---|
| atgaggtggc | tgcttctcta | ttatgctctg | tgcttctccc | tgtcaaaggc | ttcagcccac | 60 |
| accgtggagc | taaacaatat | gtttggccag | atccagtcgc | ctggttatcc | agactcctat | 120 |
| cccagtgatt | cagaggtgac | ttggaatatc | actgtcccag | atgggtttcg | gatcaagctt | 180 |
| tacttcatgc | acttcaactt | ggaatcctcc | tacctttgtg | aatatgacta | tgtgaaggta | 240 |
| gaaactgagg | accaggtgct | ggcaaccttc | tgtggcaggg | agaccacaga | cacagagcag | 300 |
| actcccggcc | aggaggtggt | cctctcccct | ggctccttca | tgtccatcac | tttccggtca | 360 |
| gatttctcca | atgaggagcg | tttcacaggc | tttgatgccc | actacatggc | tgtggatgtg | 420 |
| gacgagtgca | aggagaggga | ggacgaggag | ctgtcctgtg | accactactg | ccacaactac | 480 |
| attggcggct | actactgctc | ctgccgcttc | ggctacatcc | tccacacaga | caacaggacc | 540 |
| tgccgagtgg | agtgcagtga | aacctcttc | actcaaagga | ctggggtgat | caccagccct | 600 |
| gacttcccaa | accttaccc | caagagctct | gaatgcctgt | ataccatcga | gctggaggag | 660 |
| ggtttcatgg | tcaacctgca | gtttgaggac | atatttgaca | ttgaggacca | tcctgaggtg | 720 |
| ccctgccccct | atgactacat | caagatcaaa | gttggtccaa | aagttttggg | gccttctgt | 780 |
| ggagagaaag | ccccagaacc | catcagcacc | cagagccaca | gtgtcctgat | cctgttccat | 840 |
| agtgacaact | cggagagaa | ccggggctgg | aggctctcat | acagggctgc | aggaaatgag | 900 |
| tgcccagagc | tacagcctcc | tgtccatggg | aaaatcgagc | cctcccaagc | caagtatttc | 960 |
| ttcaaagacc | aagtgctcgt | cagctgtgac | acaggctaca | agtgctgaa | ggataatgtg | 1020 |
| gagatggaca | cattccagat | tgagtgtctg | aaggatggga | cgtggagtaa | caagattccc | 1080 |
| acctgtaaaa | ttgtagactg | tagagcccca | ggagagctgg | aacacgggct | gatcaccttc | 1140 |
| tctacaagga | acaacctcac | cacatacaag | tctgagatca | aatactcctg | tcaggagccc | 1200 |
| tattacaaga | tgctcaacaa | taacacaggt | atatatacct | gttctgccca | aggagtctgg | 1260 |
| atgaataaag | tattggggag | aagcctaccc | acctgccttc | cagtgtgtgg | gctccccaag | 1320 |
| ttctcccgga | agctgatggc | caggatcttc | aatggacgcc | cagcccagaa | aggcaccact | 1380 |
| ccctggattg | ccatgctgtc | acacctgaat | gggcagccct | tctgcggagg | ctcccttcta | 1440 |
| ggctccagct | ggatcgtgac | cgccgcacac | tgcctccacc | agtcactcga | tccggaagat | 1500 |
| ccgaccctac | gtgattcaga | cttgctcagc | ccttctgact | tcaaaatcat | cctgggcaag | 1560 |
| cattggaggc | tccggtcaga | tgaaaatgaa | cagcatctcg | gcgtcaaaca | caccactctc | 1620 |
| caccccagt | atgatcccaa | cacattcgag | aatgacgtgg | ctctggtgga | gctgttggag | 1680 |
| agccagtgc | tgaatgcctt | cgtgatgccc | atctgtctgc | ctgagggacc | ccagcaggaa | 1740 |
| ggagccatgg | tcatcgtcag | cggctggggg | aagcagttct | tgcaaaggtt | cccagagacc | 1800 |
| ctgatggaga | ttgaaatccc | gattgttgac | cacagcacct | gccagaaggc | ttatgccccg | 1860 |
| ctgaagaaga | aagtgaccag | ggacatgatc | tgtgctgggg | agaaggaagg | gggaaaggac | 1920 |
| gcctgtgcgg | gtgactctgg | aggccccatg | gtgaccctga | atagagaaag | aggccagtgg | 1980 |
| tacctggtgg | gcactgtgtc | ctggggtgat | gactgtggga | agaaggaccg | ctacggagta | 2040 |
| tactcttaca | tccaccacaa | caaggactgg | atccagaggg | tcaccggagt | gaggaac | 2097 |

<210> SEQ ID NO 3
<211> LENGTH: 699
<212> TYPE: PRT
<213> ORGANISM: Artificial

-continued

<220> FEATURE:
<223> OTHER INFORMATION: an artificially synthesized sequence

<400> SEQUENCE: 3

```
Met Arg Trp Leu Leu Leu Tyr His Ala Leu Cys Phe Ser Leu Ser Lys
1               5                   10                  15

Ala Ser Ala His Thr Val Glu Leu Asn Asp Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Asn Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
290                 295                 300

Gln Pro Pro Val His Gly Lys Ile Glu Pro Ser Gln Ala Lys Tyr Ser
305                 310                 315                 320

Phe Lys Asp Gln Val Leu Ile Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Val Thr Phe Ser Thr Arg Asn
370                 375                 380

Asn Leu Thr Thr Tyr Lys Ser Glu Ile Arg Tyr Ser Cys Gln Glu Pro
385                 390                 395                 400
```

Tyr Tyr Lys Met Leu Asn Asn Ile Thr Gly Ile Tyr Thr Cys Ser Ala
            405                 410                 415

Gln Gly Val Trp Met Asn Lys Val Leu Gly Arg Ser Leu Pro Thr Cys
        420                 425                 430

Leu Pro Val Cys Gly Leu Pro Lys Phe Ser Arg Lys Leu Met Ala Arg
            435                 440                 445

Ile Phe Asn Gly Arg Pro Ala Gln Gln Gly Thr Thr Pro Trp Ile Ala
        450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
                485                 490                 495

Asp Pro Glu Asp Pro Thr Leu Arg Asn Ser Asp Leu Leu Ser Pro Ser
            500                 505                 510

Asp Phe Lys Ile Ile Leu Gly Lys His Trp Arg Leu Gln Ser Asp Glu
        515                 520                 525

Asn Glu Gln His Leu Gly Val Lys His Ile Thr Leu His Pro Gln Tyr
    530                 535                 540

Asp Pro Ser Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
                565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
        595                 600                 605

Val Asp His Asp Thr Cys Gln Lys Ala Tyr Ala Pro Leu Lys Lys Lys
    610                 615                 620

Val Thr Arg Asp Met Ile Cys Ala Gly Glu Lys Glu Gly Gly Lys Asp
625                 630                 635                 640

Ala Cys Ala Gly Asp Ser Gly Gly Pro Met Val Thr Leu Asn Arg Glu
                645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
        675                 680                 685

Asp Trp Ile Gln Arg Val Thr Arg Leu Arg Asn
        690                 695

<210> SEQ ID NO 4
<211> LENGTH: 704
<212> TYPE: PRT
<213> ORGANISM: Mus musculus

<400> SEQUENCE: 4

Met Arg Phe Leu Ser Phe Trp Arg Leu Leu Leu Tyr His Ala Leu Cys
1               5                   10                  15

Leu Ala Leu Pro Glu Val Ser Ala His Thr Val Glu Leu Asn Glu Met
            20                  25                  30

Phe Gly Gln Ile Gln Ser Pro Gly Tyr Pro Asp Ser Tyr Pro Ser Asp
        35                  40                  45

Ser Glu Val Thr Trp Asn Ile Thr Val Pro Glu Gly Phe Arg Ile Lys
    50                  55                  60

Leu Tyr Phe Met His Phe Asn Leu Glu Ser Ser Tyr Leu Cys Glu Tyr

```
                65                  70                  75                  80
Asp Tyr Val Lys Val Glu Thr Glu Asp Gln Val Leu Ala Thr Phe Cys
                    85                  90                  95

Gly Arg Glu Thr Thr Asp Thr Glu Gln Thr Pro Gly Gln Glu Val Val
                100                 105                 110

Leu Ser Pro Gly Thr Phe Met Ser Val Thr Phe Arg Ser Asp Phe Ser
            115                 120                 125

Asn Glu Glu Arg Phe Thr Gly Phe Asp Ala His Tyr Met Ala Val Asp
        130                 135                 140

Val Asp Glu Cys Lys Glu Arg Glu Asp Glu Glu Leu Ser Cys Asp His
145                 150                 155                 160

Tyr Cys His Asn Tyr Ile Gly Gly Tyr Tyr Cys Ser Cys Arg Phe Gly
                165                 170                 175

Tyr Ile Leu His Thr Asp Asn Arg Thr Cys Arg Val Glu Cys Ser Gly
            180                 185                 190

Asn Leu Phe Thr Gln Arg Thr Gly Thr Ile Thr Ser Pro Asp Tyr Pro
        195                 200                 205

Asn Pro Tyr Pro Lys Ser Ser Glu Cys Ser Tyr Thr Ile Asp Leu Glu
    210                 215                 220

Glu Gly Phe Met Val Ser Leu Gln Phe Glu Asp Ile Phe Asp Ile Glu
225                 230                 235                 240

Asp His Pro Glu Val Pro Cys Pro Tyr Asp Tyr Ile Lys Ile Lys Ala
                245                 250                 255

Gly Ser Lys Val Trp Gly Pro Phe Cys Gly Glu Lys Ser Pro Glu Pro
            260                 265                 270

Ile Ser Thr Gln Thr His Ser Val Gln Ile Leu Phe Arg Ser Asp Asn
        275                 280                 285

Ser Gly Glu Asn Arg Gly Trp Arg Leu Ser Tyr Arg Ala Ala Gly Asn
    290                 295                 300

Glu Cys Pro Lys Leu Gln Pro Pro Val Tyr Gly Lys Ile Glu Pro Ser
305                 310                 315                 320

Gln Ala Val Tyr Ser Phe Lys Asp Gln Val Leu Val Ser Cys Asp Thr
                325                 330                 335

Gly Tyr Lys Val Leu Lys Asp Asn Glu Val Met Asp Thr Phe Gln Ile
            340                 345                 350

Glu Cys Leu Lys Asp Gly Ala Trp Ser Asn Lys Ile Pro Thr Cys Lys
        355                 360                 365

Ile Val Asp Cys Gly Ala Pro Ala Gly Leu Lys His Gly Leu Val Thr
    370                 375                 380

Phe Ser Thr Arg Asn Asn Leu Thr Thr Tyr Lys Ser Glu Ile Arg Tyr
385                 390                 395                 400

Ser Cys Gln Gln Pro Tyr Tyr Lys Met Leu His Asn Thr Thr Gly Val
                405                 410                 415

Tyr Thr Cys Ser Ala His Gly Thr Trp Thr Asn Glu Val Leu Lys Arg
            420                 425                 430

Ser Leu Pro Thr Cys Leu Pro Val Cys Gly Val Pro Lys Phe Ser Arg
        435                 440                 445

Lys Gln Ile Ser Arg Ile Phe Asn Gly Arg Pro Ala Gln Lys Gly Thr
    450                 455                 460

Met Pro Trp Ile Ala Met Leu Ser His Leu Asn Gly Gln Pro Phe Cys
465                 470                 475                 480

Gly Gly Ser Leu Leu Gly Ser Asn Trp Val Leu Thr Ala Ala His Cys
                485                 490                 495
```

```
Leu His Gln Ser Leu Asp Pro Glu Glu Pro Thr Leu His Ser Ser Tyr
            500                 505                 510

Leu Leu Ser Pro Ser Asp Phe Lys Ile Ile Met Gly Lys His Trp Arg
515                 520                 525

Arg Arg Ser Asp Glu Asp Glu Gln His Leu His Val Lys Arg Thr Thr
            530                 535                 540

Leu His Pro Leu Tyr Asn Pro Ser Thr Phe Glu Asn Asp Leu Gly Leu
545                 550                 555                 560

Val Glu Leu Ser Glu Ser Pro Arg Leu Asn Asp Phe Val Met Pro Val
                565                 570                 575

Cys Leu Pro Glu Gln Pro Ser Thr Glu Gly Thr Met Val Ile Val Ser
            580                 585                 590

Gly Trp Gly Lys Gln Phe Leu Gln Arg Phe Pro Glu Asn Leu Met Glu
                595                 600                 605

Ile Glu Ile Pro Ile Val Asn Ser Asp Thr Cys Gln Glu Ala Tyr Thr
            610                 615                 620

Pro Leu Lys Lys Lys Val Thr Lys Asp Met Ile Cys Ala Gly Glu Lys
625                 630                 635                 640

Glu Gly Gly Lys Asp Ala Cys Ala Gly Asp Ser Gly Gly Pro Met Val
                645                 650                 655

Thr Lys Asp Ala Glu Arg Asp Gln Trp Tyr Leu Val Gly Val Val Ser
            660                 665                 670

Trp Gly Glu Asp Cys Gly Lys Lys Asp Arg Tyr Gly Val Tyr Ser Tyr
                675                 680                 685

Ile Tyr Pro Asn Lys Asp Trp Ile Gln Arg Ile Thr Gly Val Arg Asn
            690                 695                 700

<210> SEQ ID NO 5
<211> LENGTH: 728
<212> TYPE: PRT
<213> ORGANISM: Homo sapiens

<400> SEQUENCE: 5

Met Arg Trp Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
                20                  25                  30

Ser Pro Gly Tyr Pro Asp Ser Tyr Pro Ser Asp Ser Glu Val Thr Trp
            35                  40                  45

Asn Ile Thr Val Pro Asp Gly Phe Arg Ile Lys Leu Tyr Phe Met His
50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
        130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
```

```
            165                 170                 175
Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
            195                 200                 205

Ser Ser Glu Cys Leu Tyr Thr Ile Glu Leu Glu Glu Gly Phe Met Val
            210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
                260                 265                 270

His Ser Val Leu Ile Leu Phe His Ser Asp Asn Ser Gly Glu Asn Arg
            275                 280                 285

Gly Trp Arg Leu Ser Tyr Arg Ala Ala Gly Asn Glu Cys Pro Glu Leu
            290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
                340                 345                 350

Gly Thr Trp Ser Asn Lys Ile Pro Thr Cys Lys Ile Val Asp Cys Arg
            355                 360                 365

Ala Pro Gly Glu Leu Glu His Gly Leu Ile Thr Phe Ser Thr Arg Asn
370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
            435                 440                 445

Arg Ile Ile Gly Gly Arg Asn Ala Glu Pro Gly Leu Phe Pro Trp Gln
450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
            515                 520                 525

Ser Gly Ala Val Asn Ser Ser Ala Ala Arg Val Val Leu His Pro Asp
530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
                580                 585                 590
```

Trp Gly Ile Ser Asn Pro Asn Val Thr Val Asp Glu Ile Ser Ser
        595                 600                 605

Gly Thr Arg Thr Leu Ser Asp Val Leu Gln Tyr Val Lys Leu Pro Val
    610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Phe Asp
            660                 665                 670

Asp Leu Ser Gln Arg Trp Val Val Gln Gly Leu Val Ser Trp Gly Gly
        675                 680                 685

Pro Glu Glu Cys Gly Ser Lys Gln Val Tyr Gly Val Tyr Thr Lys Val
    690                 695                 700

Ser Asn Tyr Val Asp Trp Val Trp Glu Gln Met Gly Leu Pro Gln Ser
705                 710                 715                 720

Val Val Glu Pro Gln Val Glu Arg
                725

<210> SEQ ID NO 6
<211> LENGTH: 429
<212> TYPE: PRT
<213> ORGANISM: Homo sapiens

<400> SEQUENCE: 6

His Thr Val Glu Leu Asn Asn Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Asp Gly Phe Arg Ile Lys Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Ile Thr Phe Arg Ser Asp Phe Ser Asn Glu Glu Arg Phe Thr Gly Phe
            100                 105                 110

Asp Ala His Tyr Met Ala Val Asp Val Asp Glu Cys Lys Glu Arg Glu
        115                 120                 125

Asp Glu Glu Leu Ser Cys Asp His Tyr Cys His Asn Tyr Ile Gly Gly
    130                 135                 140

Tyr Tyr Cys Ser Cys Arg Phe Gly Tyr Ile Leu His Thr Asp Asn Arg
145                 150                 155                 160

Thr Cys Arg Val Glu Cys Ser Asp Asn Leu Phe Thr Gln Arg Thr Gly
                165                 170                 175

Val Ile Thr Ser Pro Asp Phe Pro Asn Pro Tyr Pro Lys Ser Ser Glu
            180                 185                 190

Cys Leu Tyr Thr Ile Glu Leu Glu Glu Gly Phe Met Val Asn Leu Gln
        195                 200                 205

Phe Glu Asp Ile Phe Asp Ile Glu Asp His Pro Glu Val Pro Cys Pro
    210                 215                 220

Tyr Asp Tyr Ile Lys Ile Lys Val Gly Pro Lys Val Leu Gly Pro Phe

```
                225                 230                 235                 240
    Cys Gly Glu Lys Ala Pro Glu Pro Ile Ser Thr Gln Ser His Ser Val
                    245                 250                 255

Leu Ile Leu Phe His Ser Asp Asn Ser Gly Glu Asn Arg Gly Trp Arg
                    260                 265                 270

Leu Ser Tyr Arg Ala Ala Gly Asn Glu Cys Pro Glu Leu Gln Pro Pro
                    275                 280                 285

Val His Gly Lys Ile Glu Pro Ser Gln Ala Lys Tyr Phe Phe Lys Asp
                    290                 295                 300

Gln Val Leu Val Ser Cys Asp Thr Gly Tyr Lys Val Leu Lys Asp Asn
    305                 310                 315                 320

Val Glu Met Asp Thr Phe Gln Ile Glu Cys Leu Lys Asp Gly Thr Trp
                    325                 330                 335

Ser Asn Lys Ile Pro Thr Cys Lys Ile Val Asp Cys Arg Ala Pro Gly
                    340                 345                 350

Glu Leu Glu His Gly Leu Ile Thr Phe Ser Thr Arg Asn Asn Leu Thr
                    355                 360                 365

Thr Tyr Lys Ser Glu Ile Lys Tyr Ser Cys Gln Glu Pro Tyr Tyr Lys
                    370                 375                 380

Met Leu Asn Asn Asn Thr Gly Ile Tyr Thr Cys Ser Ala Gln Gly Val
    385                 390                 395                 400

Trp Met Asn Lys Val Leu Gly Arg Ser Leu Pro Thr Cys Leu Pro Val
                    405                 410                 415

Cys Gly Leu Pro Lys Phe Ser Arg Lys Leu Met Ala Arg
                    420                 425

<210> SEQ ID NO 7
<211> LENGTH: 251
<212> TYPE: PRT
<213> ORGANISM: Homo sapiens

<400> SEQUENCE: 7

Ile Phe Asn Gly Arg Pro Ala Gln Lys Gly Thr Thr Pro Trp Ile Ala
    1               5                   10                  15

Met Leu Ser His Leu Asn Gly Gln Pro Phe Cys Gly Gly Ser Leu Leu
                    20                  25                  30

Gly Ser Ser Trp Ile Val Thr Ala Ala His Cys Leu His Gln Ser Leu
                    35                  40                  45

Asp Pro Glu Asp Pro Thr Leu Arg Asp Ser Asp Leu Leu Ser Pro Ser
                50                  55                  60

Asp Phe Lys Ile Ile Leu Gly Lys His Trp Arg Leu Arg Ser Asp Glu
    65                  70                  75                  80

Asn Glu Gln His Leu Gly Val Lys His Thr Thr Leu His Pro Gln Tyr
                    85                  90                  95

Asp Pro Asn Thr Phe Glu Asn Asp Val Ala Leu Val Glu Leu Leu Glu
                    100                 105                 110

Ser Pro Val Leu Asn Ala Phe Val Met Pro Ile Cys Leu Pro Glu Gly
                    115                 120                 125

Pro Gln Gln Glu Gly Ala Met Val Ile Val Ser Gly Trp Gly Lys Gln
                    130                 135                 140

Phe Leu Gln Arg Phe Pro Glu Thr Leu Met Glu Ile Glu Ile Pro Ile
    145                 150                 155                 160

Val Asp His Ser Thr Cys Gln Lys Ala Tyr Ala Pro Leu Lys Lys Lys
                    165                 170                 175
```

Val Thr Arg Asp Met Ile Cys Ala Gly Glu Lys Glu Gly Lys Asp
            180                 185                 190

Ala Cys Ala Gly Asp Ser Gly Gly Pro Met Val Thr Leu Asn Arg Glu
        195                 200                 205

Arg Gly Gln Trp Tyr Leu Val Gly Thr Val Ser Trp Gly Asp Asp Cys
    210                 215                 220

Gly Lys Lys Asp Arg Tyr Gly Val Tyr Ser Tyr Ile His His Asn Lys
225                 230                 235                 240

Asp Trp Ile Gln Arg Val Thr Gly Val Arg Asn
                245                 250

<210> SEQ ID NO 8
<211> LENGTH: 251
<212> TYPE: PRT
<213> ORGANISM: Artificial
<220> FEATURE:
<223> OTHER INFORMATION: an artificially synthesized sequence

<400> SEQUENCE: 8

Ile Phe Asn Gly Arg Pro Ala Gln Gln Gly Thr Thr Pro Trp Ile Ala
1               5                   10                  15

Met Leu Ser His Leu Asn Gly Gln Pro Phe Cys Gly Gly Ser Leu Leu
            20                  25                  30

Gly Ser Ser Trp Ile Val Thr Ala Ala His Cys Leu His Gln Ser Leu
        35                  40                  45

Asp Pro Glu Asp Pro Thr Leu Arg Asn Ser Asp Leu Leu Ser Pro Ser
    50                  55                  60

Asp Phe Lys Ile Ile Leu Gly Lys His Trp Arg Leu Gln Ser Asp Glu
65                  70                  75                  80

Asn Glu Gln His Leu Gly Val Lys His Ile Thr Leu His Pro Gln Tyr
                85                  90                  95

Asp Pro Ser Thr Phe Glu Asn Asp Val Ala Leu Val Glu Leu Leu Glu
            100                 105                 110

Ser Pro Val Leu Asn Ala Phe Val Met Pro Ile Cys Leu Pro Glu Gly
        115                 120                 125

Pro Gln Gln Glu Gly Ala Met Val Ile Val Ser Gly Trp Gly Lys Gln
    130                 135                 140

Phe Leu Gln Arg Phe Pro Glu Thr Leu Met Glu Ile Glu Ile Pro Ile
145                 150                 155                 160

Val Asp His Asp Thr Cys Gln Lys Ala Tyr Ala Pro Leu Lys Lys Lys
                165                 170                 175

Val Thr Arg Asp Met Ile Cys Ala Gly Glu Lys Glu Gly Gly Lys Asp
            180                 185                 190

Ala Cys Ala Gly Asp Ser Gly Gly Pro Met Val Thr Leu Asn Arg Glu
        195                 200                 205

Arg Gly Gln Trp Tyr Leu Val Gly Thr Val Ser Trp Gly Asp Asp Cys
    210                 215                 220

Gly Lys Lys Asp Arg Tyr Gly Val Tyr Ser Tyr Ile His His Asn Lys
225                 230                 235                 240

Asp Trp Ile Gln Arg Val Thr Arg Leu Arg Asn
                245                 250

<210> SEQ ID NO 9
<211> LENGTH: 251
<212> TYPE: PRT
<213> ORGANISM: Mus musculus

<400> SEQUENCE: 9

```
Ile Phe Asn Gly Arg Pro Ala Gln Lys Gly Thr Met Pro Trp Ile Ala
1               5                   10                  15

Met Leu Ser His Leu Asn Gly Gln Pro Phe Cys Gly Gly Ser Leu Leu
            20                  25                  30

Gly Ser Asn Trp Val Leu Thr Ala Ala His Cys Leu His Gln Ser Leu
        35                  40                  45

Asp Pro Glu Pro Thr Leu His Ser Ser Tyr Leu Leu Ser Pro Ser
    50                  55                  60

Asp Phe Lys Ile Ile Met Gly Lys His Trp Arg Arg Ser Asp Glu
65                  70                  75                  80

Asp Glu Gln His Leu His Val Lys Arg Thr Thr Leu His Pro Leu Tyr
                85                  90                  95

Asn Pro Ser Thr Phe Glu Asn Asp Leu Gly Leu Val Glu Leu Ser Glu
            100                 105                 110

Ser Pro Arg Leu Asn Asp Phe Val Met Pro Val Cys Leu Pro Glu Gln
        115                 120                 125

Pro Ser Thr Glu Gly Thr Met Val Ile Val Ser Gly Trp Gly Lys Gln
    130                 135                 140

Phe Leu Gln Arg Phe Pro Glu Asn Leu Met Glu Ile Glu Ile Pro Ile
145                 150                 155                 160

Val Asn Ser Asp Thr Cys Gln Glu Ala Tyr Thr Pro Leu Lys Lys Lys
                165                 170                 175

Val Thr Lys Asp Met Ile Cys Ala Gly Glu Lys Glu Gly Gly Lys Asp
            180                 185                 190

Ala Cys Ala Gly Asp Ser Gly Gly Pro Met Val Thr Lys Asp Ala Glu
        195                 200                 205

Arg Asp Gln Trp Tyr Leu Val Gly Val Val Ser Trp Gly Glu Asp Cys
    210                 215                 220

Gly Lys Lys Asp Arg Tyr Gly Val Tyr Ser Tyr Ile Tyr Pro Asn Lys
225                 230                 235                 240

Asp Trp Ile Gln Arg Ile Thr Gly Val Arg Asn
                245                 250
```

<210> SEQ ID NO 10
<211> LENGTH: 430
<212> TYPE: PRT
<213> ORGANISM: Homo sapiens

<400> SEQUENCE: 10

```
His Thr Val Glu Leu Asn Asn Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Asp Gly Phe Arg Ile Lys Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Ile Thr Phe Arg Ser Asp Phe Ser Asn Glu Glu Arg Phe Thr Gly Phe
            100                 105                 110
```

Asp Ala His Tyr Met Ala Val Asp Val Asp Glu Cys Lys Glu Arg Glu
            115                 120                 125

Asp Glu Glu Leu Ser Cys Asp His Tyr Cys His Asn Tyr Ile Gly Gly
        130                 135                 140

Tyr Tyr Cys Ser Cys Arg Phe Gly Tyr Ile Leu His Thr Asp Asn Arg
145                 150                 155                 160

Thr Cys Arg Val Glu Cys Ser Asp Asn Leu Phe Thr Gln Arg Thr Gly
                165                 170                 175

Val Ile Thr Ser Pro Asp Phe Pro Asn Pro Tyr Pro Lys Ser Ser Glu
            180                 185                 190

Cys Leu Tyr Thr Ile Glu Leu Glu Glu Gly Phe Met Val Asn Leu Gln
        195                 200                 205

Phe Glu Asp Ile Phe Asp Ile Glu Asp His Pro Glu Val Pro Cys Pro
210                 215                 220

Tyr Asp Tyr Ile Lys Ile Lys Val Gly Pro Lys Val Leu Gly Pro Phe
225                 230                 235                 240

Cys Gly Glu Lys Ala Pro Glu Pro Ile Ser Thr Gln Ser His Ser Val
                245                 250                 255

Leu Ile Leu Phe His Ser Asp Asn Ser Gly Glu Asn Arg Gly Trp Arg
            260                 265                 270

Leu Ser Tyr Arg Ala Ala Gly Asn Glu Cys Pro Glu Leu Gln Pro Pro
        275                 280                 285

Val His Gly Lys Ile Glu Pro Ser Gln Ala Lys Tyr Phe Phe Lys Asp
        290                 295                 300

Gln Val Leu Val Ser Cys Asp Thr Gly Tyr Lys Val Leu Lys Asp Asn
305                 310                 315                 320

Val Glu Met Asp Thr Phe Gln Ile Glu Cys Leu Lys Asp Gly Thr Trp
                325                 330                 335

Ser Asn Lys Ile Pro Thr Cys Lys Ile Val Asp Cys Arg Ala Pro Gly
            340                 345                 350

Glu Leu Glu His Gly Leu Ile Thr Phe Ser Thr Arg Asn Asn Leu Thr
        355                 360                 365

Thr Tyr Lys Ser Glu Ile Lys Tyr Ser Cys Gln Glu Pro Tyr Tyr Lys
370                 375                 380

Met Leu Asn Asn Asn Thr Gly Ile Tyr Thr Cys Ser Ala Gln Gly Val
385                 390                 395                 400

Trp Met Asn Lys Val Leu Gly Arg Ser Leu Pro Thr Cys Leu Pro Glu
                405                 410                 415

Cys Gly Gln Pro Ser Arg Ser Leu Pro Ser Leu Val Lys Arg
            420                 425                 430

<210> SEQ ID NO 11
<211> LENGTH: 279
<212> TYPE: PRT
<213> ORGANISM: Homo sapiens

<400> SEQUENCE: 11

Ile Ile Gly Gly Arg Asn Ala Glu Pro Gly Leu Phe Pro Trp Gln Ala
1               5                   10                  15

Leu Ile Val Val Glu Asp Thr Ser Arg Val Pro Asn Asp Lys Trp Phe
            20                  25                  30

Gly Ser Gly Ala Leu Leu Ser Ala Ser Trp Ile Leu Thr Ala Ala His
        35                  40                  45

Val Leu Arg Ser Gln Arg Arg Asp Thr Thr Val Ile Pro Val Ser Lys
    50                  55                  60

```
Glu His Val Thr Val Tyr Leu Gly Leu His Asp Val Arg Asp Lys Ser
 65                  70                  75                  80

Gly Ala Val Asn Ser Ser Ala Ala Arg Val Leu His Pro Asp Phe
             85                  90                  95

Asn Ile Gln Asn Tyr Asn His Asp Ile Ala Leu Val Gln Leu Gln Glu
            100                 105                 110

Pro Val Pro Leu Gly Pro His Val Met Pro Val Cys Leu Pro Arg Leu
            115                 120                 125

Glu Pro Glu Gly Pro Ala Pro His Met Leu Gly Leu Val Ala Gly Trp
130                 135                 140

Gly Ile Ser Asn Pro Asn Val Thr Val Asp Glu Ile Ile Ser Ser Gly
145                 150                 155                 160

Thr Arg Thr Leu Ser Asp Val Leu Gln Tyr Val Lys Leu Pro Val Val
                165                 170                 175

Pro His Ala Glu Cys Lys Thr Ser Tyr Glu Ser Arg Ser Gly Asn Tyr
            180                 185                 190

Ser Val Thr Glu Asn Met Phe Cys Ala Gly Tyr Tyr Glu Gly Gly Lys
            195                 200                 205

Asp Thr Cys Leu Gly Asp Ser Gly Gly Ala Phe Val Ile Phe Asp Asp
210                 215                 220

Leu Ser Gln Arg Trp Val Val Gln Gly Leu Val Ser Trp Gly Gly Pro
225                 230                 235                 240

Glu Glu Cys Gly Ser Lys Gln Val Tyr Gly Val Tyr Thr Lys Val Ser
                245                 250                 255

Asn Tyr Val Asp Trp Val Trp Glu Gln Met Gly Leu Pro Gln Ser Val
            260                 265                 270

Val Glu Pro Gln Val Glu Arg
            275

<210> SEQ ID NO 12
<211> LENGTH: 686
<212> TYPE: PRT
<213> ORGANISM: Homo sapiens

<400> SEQUENCE: 12

Met Arg Leu Leu Thr Leu Leu Gly Leu Leu Cys Gly Ser Val Ala Thr
 1               5                  10                  15

Pro Leu Gly Pro Lys Trp Pro Glu Pro Val Phe Gly Arg Leu Ala Ser
             20                  25                  30

Pro Gly Phe Pro Gly Glu Tyr Ala Asn Asp Gln Glu Arg Arg Trp Thr
         35                  40                  45

Leu Thr Ala Pro Pro Gly Tyr Arg Leu Arg Leu Tyr Phe Thr His Phe
     50                  55                  60

Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
             85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
        130                 135                 140

Ala Pro Gly Glu Ala Pro Thr Cys Asp His His Cys His Asn His Leu
```

```
                145                 150                 155                 160
Gly Gly Phe Tyr Cys Ser Cys Arg Ala Gly Tyr Val Leu His Arg Asn
                    165                 170                 175
Lys Arg Thr Cys Ser Ala Leu Cys Ser Gly Gln Val Phe Thr Gln Arg
                    180                 185                 190
Ser Gly Glu Leu Ser Ser Pro Glu Tyr Pro Arg Pro Tyr Pro Lys Leu
                    195                 200                 205
Ser Ser Cys Thr Tyr Ser Ile Ser Leu Glu Glu Gly Phe Ser Val Ile
                    210                 215                 220
Leu Asp Phe Val Glu Ser Phe Asp Val Glu Thr His Pro Glu Thr Leu
225                 230                 235                 240
Cys Pro Tyr Asp Phe Leu Lys Ile Gln Thr Asp Arg Glu Glu His Gly
                    245                 250                 255
Pro Phe Cys Gly Lys Thr Leu Pro His Arg Ile Glu Thr Lys Ser Asn
                    260                 265                 270
Thr Val Thr Ile Thr Phe Val Thr Asp Glu Ser Gly Asp His Thr Gly
                    275                 280                 285
Trp Lys Ile His Tyr Thr Ser Thr Ala Gln Pro Cys Pro Tyr Pro Met
                    290                 295                 300
Ala Pro Pro Asn Gly His Val Ser Pro Val Gln Ala Lys Tyr Ile Leu
305                 310                 315                 320
Lys Asp Ser Phe Ser Ile Phe Cys Glu Thr Gly Tyr Glu Leu Leu Gln
                    325                 330                 335
Gly His Leu Pro Leu Lys Ser Phe Thr Ala Val Cys Gln Lys Asp Gly
                    340                 345                 350
Ser Trp Asp Arg Pro Met Pro Ala Cys Ser Ile Val Asp Cys Gly Pro
                    355                 360                 365
Pro Asp Asp Leu Pro Ser Gly Arg Val Glu Tyr Ile Thr Gly Pro Gly
                    370                 375                 380
Val Thr Thr Tyr Lys Ala Val Ile Gln Tyr Ser Cys Glu Glu Thr Phe
385                 390                 395                 400
Tyr Thr Met Lys Val Asn Asp Gly Lys Tyr Val Cys Glu Ala Asp Gly
                    405                 410                 415
Phe Trp Thr Ser Ser Lys Gly Glu Lys Ser Leu Pro Val Cys Glu Pro
                    420                 425                 430
Val Cys Gly Leu Ser Ala Arg Thr Thr Gly Gly Arg Ile Tyr Gly Gly
                    435                 440                 445
Gln Lys Ala Lys Pro Gly Asp Phe Pro Trp Gln Val Leu Ile Leu Gly
                    450                 455                 460
Gly Thr Thr Ala Ala Gly Ala Leu Leu Tyr Asp Asn Trp Val Leu Thr
465                 470                 475                 480
Ala Ala His Ala Val Tyr Glu Gln Lys His Asp Ala Ser Ala Leu Asp
                    485                 490                 495
Ile Arg Met Gly Thr Leu Lys Arg Leu Ser Pro His Tyr Thr Gln Ala
                    500                 505                 510
Trp Ser Glu Ala Val Phe Ile His Glu Gly Tyr Thr His Asp Ala Gly
                    515                 520                 525
Phe Asp Asn Asp Ile Ala Leu Ile Lys Leu Asn Asn Lys Val Val Ile
                    530                 535                 540
Asn Ser Asn Ile Thr Pro Ile Cys Leu Pro Arg Lys Glu Ala Glu Ser
545                 550                 555                 560
Phe Met Arg Thr Asp Asp Ile Gly Thr Ala Ser Gly Trp Gly Leu Thr
                    565                 570                 575
```

```
Gln Arg Gly Phe Leu Ala Arg Asn Leu Met Tyr Val Asp Ile Pro Ile
                580                 585                 590

Val Asp His Gln Lys Cys Thr Ala Ala Tyr Glu Lys Pro Pro Tyr Pro
            595                 600                 605

Arg Gly Ser Val Thr Ala Asn Met Leu Cys Ala Gly Leu Glu Ser Gly
        610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Ile Val Ser Trp Gly
                645                 650                 655

Ser Met Asn Cys Gly Glu Ala Gly Gln Tyr Gly Val Tyr Thr Lys Val
                660                 665                 670

Ile Asn Tyr Ile Pro Trp Ile Glu Asn Ile Ile Ser Asp Phe
            675                 680                 685

<210> SEQ ID NO 13
<211> LENGTH: 429
<212> TYPE: PRT
<213> ORGANISM: Homo sapiens

<400> SEQUENCE: 13

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
130                 135                 140

Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175

Arg Ser Gly Glu Leu Ser Ser Pro Glu Tyr Pro Arg Pro Tyr Pro Lys
            180                 185                 190

Leu Ser Ser Cys Thr Tyr Ser Ile Ser Leu Glu Glu Gly Phe Ser Val
        195                 200                 205

Ile Leu Asp Phe Val Glu Ser Phe Asp Val Glu Thr His Pro Glu Thr
    210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
```

```
                        260                 265                 270
Gly Trp Lys Ile His Tyr Thr Ser Thr Ala Gln Pro Cys Pro Tyr Pro
                275                 280                 285

Met Ala Pro Pro Asn Gly His Val Ser Pro Val Gln Ala Lys Tyr Ile
            290                 295                 300

Leu Lys Asp Ser Phe Ser Ile Phe Cys Glu Thr Gly Tyr Glu Leu Leu
305                 310                 315                 320

Gln Gly His Leu Pro Leu Lys Ser Phe Thr Ala Val Cys Gln Lys Asp
                325                 330                 335

Gly Ser Trp Asp Arg Pro Met Pro Ala Cys Ser Ile Val Asp Cys Gly
            340                 345                 350

Pro Pro Asp Asp Leu Pro Ser Gly Arg Val Glu Tyr Ile Thr Gly Pro
            355                 360                 365

Gly Val Thr Thr Tyr Lys Ala Val Ile Gln Tyr Ser Cys Glu Glu Thr
            370                 375                 380

Phe Tyr Thr Met Lys Val Asn Asp Gly Lys Tyr Val Cys Glu Ala Asp
385                 390                 395                 400

Gly Phe Trp Thr Ser Ser Lys Gly Glu Lys Ser Leu Pro Val Cys Glu
                405                 410                 415

Pro Val Cys Gly Leu Ser Ala Arg Thr Thr Gly Gly Arg
                420                 425

<210> SEQ ID NO 14
<211> LENGTH: 242
<212> TYPE: PRT
<213> ORGANISM: Homo sapiens

<400> SEQUENCE: 14

Ile Tyr Gly Gly Gln Lys Ala Lys Pro Gly Asp Phe Pro Trp Gln Val
1               5                   10                  15

Leu Ile Leu Gly Gly Thr Thr Ala Ala Gly Ala Leu Leu Tyr Asp Asn
                20                  25                  30

Trp Val Leu Thr Ala Ala His Ala Val Tyr Glu Gln Lys His Asp Ala
            35                  40                  45

Ser Ala Leu Asp Ile Arg Met Gly Thr Leu Lys Arg Leu Ser Pro His
        50                  55                  60

Tyr Thr Gln Ala Trp Ser Glu Ala Val Phe Ile His Glu Gly Tyr Thr
65                  70                  75                  80

His Asp Ala Gly Phe Asp Asn Asp Ile Ala Leu Ile Lys Leu Asn Asn
                85                  90                  95

Lys Val Val Ile Asn Ser Asn Ile Thr Pro Ile Cys Leu Pro Arg Lys
                100                 105                 110

Glu Ala Glu Ser Phe Met Arg Thr Asp Asp Ile Gly Thr Ala Ser Gly
            115                 120                 125

Trp Gly Leu Thr Gln Arg Gly Phe Leu Ala Arg Asn Leu Met Tyr Val
130                 135                 140

Asp Ile Pro Ile Val Asp His Gln Lys Cys Thr Ala Ala Tyr Glu Lys
145                 150                 155                 160

Pro Pro Tyr Pro Arg Gly Ser Val Thr Ala Asn Met Leu Cys Ala Gly
                165                 170                 175

Leu Glu Ser Gly Gly Lys Asp Ser Cys Arg Gly Asp Ser Gly Gly Ala
            180                 185                 190

Leu Val Phe Leu Asp Ser Glu Thr Glu Arg Trp Phe Val Gly Gly Ile
            195                 200                 205
```

```
Val Ser Trp Gly Ser Met Asn Cys Gly Glu Ala Gly Gln Tyr Gly Val
210                 215                 220

Tyr Thr Lys Val Ile Asn Tyr Ile Pro Trp Ile Glu Asn Ile Ile Ser
225                 230                 235                 240

Asp Phe

<210> SEQ ID NO 15
<211> LENGTH: 429
<212> TYPE: PRT
<213> ORGANISM: Homo sapiens

<400> SEQUENCE: 15

Met Arg Trp Leu Leu Leu Tyr Tyr Ala Leu Cys Phe Ser Leu Ser Lys
1               5                   10                  15

Ala Ser Ala Asp Tyr Lys Asp Asp Asp Lys Gly Asn Glu Cys Pro
            20                  25                  30

Glu Leu Gln Pro Pro Val His Gly Lys Ile Glu Pro Ser Gln Ala Lys
                35                  40                  45

Tyr Phe Phe Lys Asp Gln Val Leu Val Ser Cys Asp Thr Gly Tyr Lys
    50                  55                  60

Val Leu Lys Asp Asn Val Glu Met Asp Thr Phe Gln Ile Glu Cys Leu
65                  70                  75                  80

Lys Asp Gly Thr Trp Ser Asn Lys Ile Pro Thr Cys Lys Ile Val Asp
                85                  90                  95

Cys Arg Ala Pro Gly Glu Leu Glu His Gly Leu Ile Thr Phe Ser Thr
            100                 105                 110

Arg Asn Asn Leu Thr Thr Tyr Lys Ser Glu Ile Lys Tyr Ser Cys Gln
        115                 120                 125

Glu Pro Tyr Tyr Lys Met Leu Asn Asn Asn Thr Gly Ile Tyr Thr Cys
    130                 135                 140

Ser Ala Gln Gly Val Trp Met Asn Lys Val Leu Gly Arg Ser Leu Pro
145                 150                 155                 160

Thr Cys Leu Pro Val Cys Gly Leu Pro Lys Phe Ser Arg Lys Leu Met
                165                 170                 175

Ala Arg Ile Phe Asn Gly Arg Pro Ala Gln Lys Gly Thr Thr Pro Trp
            180                 185                 190

Ile Ala Met Leu Ser His Leu Asn Gly Gln Pro Phe Cys Gly Gly Ser
        195                 200                 205

Leu Leu Gly Ser Ser Trp Ile Val Thr Ala Ala His Cys Leu His Gln
210                 215                 220

Ser Leu Asp Pro Glu Asp Pro Thr Leu Arg Asp Ser Asp Leu Leu Ser
225                 230                 235                 240

Pro Ser Asp Phe Lys Ile Ile Leu Gly Lys His Trp Arg Leu Arg Ser
                245                 250                 255

Asp Glu Asn Glu Gln His Leu Gly Val Lys His Thr Thr Leu His Pro
            260                 265                 270

Gln Tyr Asp Pro Asn Thr Phe Glu Asn Asp Val Ala Leu Val Glu Leu
        275                 280                 285

Leu Glu Ser Pro Val Leu Asn Ala Phe Val Met Pro Ile Cys Leu Pro
    290                 295                 300

Glu Gly Pro Gln Gln Glu Gly Ala Met Val Ile Val Ser Gly Trp Gly
305                 310                 315                 320

Lys Gln Phe Leu Gln Arg Phe Pro Glu Thr Leu Met Glu Ile Glu Ile
                325                 330                 335
```

```
Pro Ile Val Asp His Ser Thr Cys Gln Lys Ala Tyr Ala Pro Leu Lys
                340                 345                 350

Lys Lys Val Thr Arg Asp Met Ile Cys Ala Gly Glu Lys Glu Gly Gly
        355                 360                 365

Lys Asp Ala Cys Ala Gly Asp Ser Gly Gly Pro Met Val Thr Leu Asn
    370                 375                 380

Arg Glu Arg Gly Gln Trp Tyr Leu Val Gly Thr Val Ser Trp Gly Asp
385                 390                 395                 400

Asp Cys Gly Lys Lys Asp Arg Tyr Gly Val Tyr Ser Tyr Ile His His
                405                 410                 415

Asn Lys Asp Trp Ile Gln Arg Val Thr Gly Val Arg Asn
                420                 425

<210> SEQ ID NO 16
<211> LENGTH: 429
<212> TYPE: PRT
<213> ORGANISM: Homo sapiens

<400> SEQUENCE: 16

Met Arg Trp Leu Leu Leu Tyr Tyr Ala Leu Cys Phe Ser Leu Ser Lys
1               5                   10                  15

Ala Ser Ala Asp Tyr Lys Asp Asp Asp Lys Gly Asn Glu Cys Pro
                20                  25                  30

Glu Leu Gln Pro Pro Val His Gly Lys Ile Glu Pro Ser Gln Ala Lys
            35                  40                  45

Tyr Phe Phe Lys Asp Gln Val Leu Val Ser Cys Asp Thr Gly Tyr Lys
        50                  55                  60

Val Leu Lys Asp Asn Val Glu Met Asp Thr Phe Gln Ile Glu Cys Leu
65                  70                  75                  80

Lys Asp Gly Thr Trp Ser Asn Lys Ile Pro Thr Cys Lys Ile Val Asp
                85                  90                  95

Cys Arg Ala Pro Gly Glu Leu Glu His Gly Leu Ile Thr Phe Ser Thr
            100                 105                 110

Arg Asn Asn Leu Thr Thr Tyr Lys Ser Glu Ile Lys Tyr Ser Cys Gln
        115                 120                 125

Glu Pro Tyr Tyr Lys Met Leu Asn Asn Asn Thr Gly Ile Tyr Thr Cys
    130                 135                 140

Ser Ala Gln Gly Val Trp Met Asn Lys Val Leu Gly Arg Ser Leu Pro
145                 150                 155                 160

Thr Cys Leu Pro Val Cys Gly Leu Pro Lys Phe Ser Arg Lys Leu Met
                165                 170                 175

Ala Arg Ile Phe Asn Gly Arg Pro Ala Gln Lys Gly Thr Thr Pro Trp
            180                 185                 190

Ile Ala Met Leu Ser His Leu Asn Gly Gln Pro Phe Cys Gly Gly Ser
        195                 200                 205

Leu Leu Gly Ser Ser Trp Ile Val Thr Ala Ala His Cys Leu His Gln
    210                 215                 220

Ser Leu Asp Pro Glu Asp Pro Thr Leu Arg Asp Ser Asp Leu Leu Ser
225                 230                 235                 240

Pro Ser Asp Phe Lys Ile Ile Leu Gly Lys His Trp Arg Leu Arg Ser
                245                 250                 255

Asp Glu Asn Glu Gln His Leu Gly Val Lys His Thr Thr Leu His Pro
            260                 265                 270

Gln Tyr Asp Pro Asn Thr Phe Glu Asn Asp Val Ala Leu Val Glu Leu
        275                 280                 285
```

-continued

```
Leu Glu Ser Pro Val Leu Asn Ala Phe Val Met Pro Ile Cys Leu Pro
    290                 295                 300

Glu Gly Pro Gln Gln Glu Gly Ala Met Val Ile Val Ser Gly Trp Gly
305                 310                 315                 320

Lys Gln Phe Leu Gln Arg Phe Pro Glu Thr Leu Met Glu Ile Glu Ile
                325                 330                 335

Pro Ile Val Asp His Ser Thr Cys Gln Lys Ala Tyr Ala Pro Leu Lys
            340                 345                 350

Lys Lys Val Thr Arg Asp Met Ile Cys Ala Gly Glu Lys Glu Gly Gly
        355                 360                 365

Lys Asp Ala Cys Ala Gly Asp Ala Gly Gly Pro Met Val Thr Leu Asn
    370                 375                 380

Arg Glu Arg Gly Gln Trp Tyr Leu Val Gly Thr Val Ser Trp Gly Asp
385                 390                 395                 400

Asp Cys Gly Lys Lys Asp Arg Tyr Gly Val Tyr Ser Tyr Ile His His
                405                 410                 415

Asn Lys Asp Trp Ile Gln Arg Val Thr Gly Val Arg Asn
            420                 425

<210> SEQ ID NO 17
<211> LENGTH: 458
<212> TYPE: PRT
<213> ORGANISM: Homo sapiens

<400> SEQUENCE: 17

Met Arg Trp Leu Leu Tyr Tyr Ala Leu Cys Phe Ser Leu Ser Lys
1               5                   10                  15

Ala Ser Ala Asp Tyr Lys Asp Asp Asp Lys Gly Asn Glu Cys Pro
            20                  25                  30

Glu Leu Gln Pro Pro Val His Gly Lys Ile Glu Pro Ser Gln Ala Lys
        35                  40                  45

Tyr Phe Phe Lys Asp Gln Val Leu Val Ser Cys Asp Thr Gly Tyr Lys
    50                  55                  60

Val Leu Lys Asp Asn Val Glu Met Asp Thr Phe Gln Ile Glu Cys Leu
65                  70                  75                  80

Lys Asp Gly Thr Trp Ser Asn Lys Ile Pro Thr Cys Lys Ile Val Asp
                85                  90                  95

Cys Arg Ala Pro Gly Glu Leu Glu His Gly Leu Ile Thr Phe Ser Thr
            100                 105                 110

Arg Asn Asn Leu Thr Thr Tyr Lys Ser Glu Ile Lys Tyr Ser Cys Gln
        115                 120                 125

Glu Pro Tyr Tyr Lys Met Leu Asn Asn Asn Thr Gly Ile Tyr Thr Cys
    130                 135                 140

Ser Ala Gln Gly Val Trp Met Asn Lys Val Leu Gly Arg Ser Leu Pro
145                 150                 155                 160

Thr Cys Leu Pro Glu Cys Gly Gln Pro Ser Arg Ser Leu Pro Ser Leu
                165                 170                 175

Val Lys Arg Ile Ile Gly Gly Arg Asn Ala Glu Pro Gly Leu Phe Pro
            180                 185                 190

Trp Gln Ala Leu Ile Val Val Glu Asp Thr Ser Arg Val Pro Asn Asp
        195                 200                 205

Lys Trp Phe Gly Ser Gly Ala Leu Leu Ser Ala Ser Trp Ile Leu Thr
    210                 215                 220

Ala Ala His Val Leu Arg Ser Gln Arg Arg Asp Thr Thr Val Ile Pro
```

```
                225                 230                 235                 240
Val Ser Lys Glu His Val Thr Val Tyr Leu Gly Leu His Asp Val Arg
                245                 250                 255
Asp Lys Ser Gly Ala Val Asn Ser Ser Ala Arg Val Val Leu His
                260                 265                 270
Pro Asp Phe Asn Ile Gln Asn Tyr Asn His Asp Ile Ala Leu Val Gln
                275                 280                 285
Leu Gln Glu Pro Val Pro Leu Gly Pro His Val Met Pro Val Cys Leu
                290                 295                 300
Pro Arg Leu Glu Pro Glu Gly Pro Ala Pro His Met Leu Gly Leu Val
305                 310                 315                 320
Ala Gly Trp Gly Ile Ser Asn Pro Asn Val Thr Val Asp Glu Ile Ile
                325                 330                 335
Ser Ser Gly Thr Arg Thr Leu Ser Asp Val Leu Gln Tyr Val Lys Leu
                340                 345                 350
Pro Val Val Pro His Ala Glu Cys Lys Thr Ser Tyr Glu Ser Arg Ser
                355                 360                 365
Gly Asn Tyr Ser Val Thr Glu Asn Met Phe Cys Ala Gly Tyr Tyr Glu
                370                 375                 380
Gly Gly Lys Asp Thr Cys Leu Gly Asp Ala Gly Gly Ala Phe Val Ile
385                 390                 395                 400
Phe Asp Asp Leu Ser Gln Arg Trp Val Val Gln Gly Leu Val Ser Trp
                405                 410                 415
Gly Gly Pro Glu Glu Cys Gly Ser Lys Gln Val Tyr Gly Val Tyr Thr
                420                 425                 430
Lys Val Ser Asn Tyr Val Asp Trp Val Trp Glu Gln Met Gly Leu Pro
                435                 440                 445
Gln Ser Val Val Glu Pro Gln Val Glu Arg
                450                 455

<210> SEQ ID NO 18
<211> LENGTH: 325
<212> TYPE: PRT
<213> ORGANISM: Artificial
<220> FEATURE:
<223> OTHER INFORMATION: an artificially synthesized sequence

<400> SEQUENCE: 18

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
                100                 105                 110
Glu Phe Arg Gly Gly Pro Lys Val Phe Leu Phe Pro Pro Lys Pro Lys
                115                 120                 125
Asp Thr Leu Met Ile Ser Arg Thr Pro Glu Val Thr Cys Val Val Val
```

```
                130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu
                325

<210> SEQ ID NO 19
<211> LENGTH: 107
<212> TYPE: PRT
<213> ORGANISM: Artificial
<220> FEATURE:
<223> OTHER INFORMATION: an artificially synthesized sequence

<400> SEQUENCE: 19

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Cys
                50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 20
<211> LENGTH: 124
<212> TYPE: PRT
<213> ORGANISM: Oryctolagus cuniculus

<400> SEQUENCE: 20

Gln Ser Val Glu Glu Ser Gly Gly Arg Leu Val Thr Pro Gly Thr Pro
1               5                   10                  15
```

```
Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
        35                  40                  45

Ile Ile Thr Asn Leu Asp Asn Thr Tyr Tyr Ala Asn Trp Ala Lys Gly
    50                  55                  60

Arg Phe Thr Ile Ser Lys Thr Ser Thr Val Asp Leu Lys Ile Thr
65                  70                  75                  80

Ser Pro Thr Thr Glu Asp Thr Ala Ala Tyr Leu Cys Ala Arg Glu Arg
                85                  90                  95

Ile Lys Arg Lys Tyr Ser Tyr Asp Asp Tyr Gly Gly Trp Ala Phe Asp
                100                 105                 110

Pro Trp Gly Pro Gly Thr Leu Val Thr Val Ser Ser
            115                 120
```

<210> SEQ ID NO 21
<211> LENGTH: 109
<212> TYPE: PRT
<213> ORGANISM: Oryctolagus cuniculus

<400> SEQUENCE: 21

```
Gln Val Leu Thr Gln Thr Pro Ser Ser Val Ser Gly Pro Val Gly Gly
1               5                   10                  15

Thr Val Thr Ile Asn Cys Gln Ala Ile Glu Asn Ile Tyr Arg Ser Leu
            20                  25                  30

Ala Trp Tyr Gln Gln Lys Pro Gly Gln Pro Pro Lys Leu Leu Ile Tyr
        35                  40                  45

Asp Thr Ser Asp Leu Ala Ser Gly Val Pro Ser Arg Phe Ser Gly Ser
    50                  55                  60

Gly Ser Gly Thr Glu Tyr Thr Leu Thr Ile Ser Gly Val Gln Cys Asp
65                  70                  75                  80

Asp Ala Ala Thr Tyr Tyr Cys Gln Ser Tyr Tyr Tyr Ser Ser Val Thr
                85                  90                  95

Tyr Asn Ala Phe Gly Gly Gly Thr Lys Val Glu Ile Lys
                100                 105
```

<210> SEQ ID NO 22
<211> LENGTH: 120
<212> TYPE: PRT
<213> ORGANISM: Oryctolagus cuniculus

<400> SEQUENCE: 22

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Asp Ile Asn Asn Tyr Ala
            20                  25                  30

Ile His Trp Val Arg Gln Ala Pro Gly Glu Gly Leu Glu Trp Ile Gly
        35                  40                  45

Tyr Ile Tyr Ala Arg Ser Gly Val Thr Trp Tyr Ala Ser Trp Val Lys
    50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Val
                85                  90                  95

Leu Ala Gly Gly Gly Tyr Ala Asn Thr Gly Leu Ser Leu Trp Gly Pro
                100                 105                 110
```

```
Gly Thr Leu Val Thr Val Ser Ser
        115                 120

<210> SEQ ID NO 23
<211> LENGTH: 112
<212> TYPE: PRT
<213> ORGANISM: Oryctolagus cuniculus

<400> SEQUENCE: 23

Ala Asp Ile Val Met Thr Gln Thr Pro Ser Ser Val Ser Ala Ala Val
1               5                   10                  15

Gly Gly Thr Val Thr Ile Lys Cys Gln Ala Ser Gln Asn Ile Gly Tyr
            20                  25                  30

Ser Ser Ala Trp Tyr Gln Gln Lys Pro Gly Gln Arg Pro Lys Leu Met
        35                  40                  45

Ile Tyr Gly Ala Ser Thr Leu Ala Ser Gly Val Pro Ser Arg Phe Ser
    50                  55                  60

Gly Ser Gly Ser Gly Thr Glu Tyr Thr Leu Thr Ile Ser Gly Val Gln
65                  70                  75                  80

Cys Asp Asp Ala Ala Thr Tyr Tyr Cys Gln Ser Asn Tyr Ile Ser Ser
                85                  90                  95

Gly Ser Val Asp Gly Thr Phe Gly Gly Gly Thr Lys Val Glu Ile Lys
            100                 105                 110

<210> SEQ ID NO 24
<211> LENGTH: 122
<212> TYPE: PRT
<213> ORGANISM: Oryctolagus cuniculus

<400> SEQUENCE: 24

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Cys Tyr
            20                  25                  30

Met Ser Trp Val Arg Gln Ala Pro Gly Glu Gly Leu Glu Trp Ile Gly
        35                  40                  45

Thr Ile Tyr Thr Gly Ser Gly Ala Thr Tyr Tyr Ala Ser Trp Ala Lys
    50                  55                  60

Gly Arg Phe Thr Val Ser Ile Thr Ser Thr Thr Val Asp Leu Lys Ile
65                  70                  75                  80

Thr Ser Pro Thr Thr Glu Asp Thr Ala Thr Tyr Phe Cys Ala Arg Ala
                85                  90                  95

Ile Tyr Pro Gly Ser Ser Ser Asn Leu Cys Ala Phe Asp Leu Trp
            100                 105                 110

Gly Pro Gly Thr Leu Val Thr Val Ser Ser
        115                 120

<210> SEQ ID NO 25
<211> LENGTH: 109
<212> TYPE: PRT
<213> ORGANISM: Oryctolagus cuniculus

<400> SEQUENCE: 25

Gln Val Leu Thr Gln Thr Pro Ala Ser Val Ser Ala Ala Val Gly Gly
1               5                   10                  15

Thr Val Thr Ile Asn Cys Gln Ala Ser Gln Ser Val Tyr Asp Asn Asn
            20                  25                  30
```

```
Trp Leu Ala Trp Tyr Gln Gln Lys Pro Gly Gln Pro Pro Lys Leu Leu
            35                  40                  45

Ile Tyr Gln Ala Ser Ser Leu Ala Ser Gly Val Pro Ser Arg Phe Lys
 50                  55                  60

Gly Ser Gly Ser Gly Ala Gln Phe Thr Leu Thr Ile Ser Asp Leu Glu
 65                  70                  75                  80

Cys Asp Asp Ala Ala Thr Tyr Phe Cys Gln Gly Tyr Tyr Ala Gly Val
                 85                  90                  95

Leu Tyr Ser Phe Gly Gly Gly Thr Lys Val Glu Ile Lys
                100                 105
```

<210> SEQ ID NO 26
<211> LENGTH: 119
<212> TYPE: PRT
<213> ORGANISM: Oryctolagus cuniculus

<400> SEQUENCE: 26

```
Gln Ser Val Glu Glu Ser Gly Gly Arg Leu Val Thr Pro Gly Thr Pro
 1               5                  10                  15

Leu Thr Leu Thr Cys Thr Ala Ser Gly Phe Ser Leu Ile Asn Tyr Tyr
                20                  25                  30

Met Thr Trp Val Arg Gln Ala Pro Gly Lys Gly Leu Glu Trp Ile Gly
            35                  40                  45

Ile Ile Asn Thr Asp Gly Gly Thr Tyr Tyr Ala Ser Trp Ala Lys Gly
 50                  55                  60

Arg Phe Thr Ile Ser Arg Thr Ser Thr Thr Val Asp Leu Lys Met Thr
 65                  70                  75                  80

Ser Leu Thr Thr Glu Asp Thr Ala Thr Tyr Phe Cys Ala Arg Gly Val
                 85                  90                  95

Phe Thr Gly Gly Trp Thr Gly Met Arg Thr Asn Leu Trp Gly Pro Gly
                100                 105                 110

Thr Leu Val Thr Val Ser Ser
            115
```

<210> SEQ ID NO 27
<211> LENGTH: 109
<212> TYPE: PRT
<213> ORGANISM: Oryctolagus cuniculus

<400> SEQUENCE: 27

```
Asp Val Val Met Thr Gln Thr Pro Ala Ser Val Glu Ala Ala Val Gly
 1               5                  10                  15

Gly Thr Val Thr Ile Lys Cys Gln Ala Ser Glu Asp Ile Tyr Ile Leu
                20                  25                  30

Leu Ala Trp Tyr Gln Gln Lys Pro Gly Gln Pro Pro Lys Leu Leu Ile
            35                  40                  45

Tyr Ala Ala Ser Asn Leu Glu Ser Gly Val Pro Ser Arg Phe Lys Gly
 50                  55                  60

Ser Gly Ser Gly Thr Glu Phe Thr Leu Thr Ile Ser Asp Leu Glu Cys
 65                  70                  75                  80

Ala Asp Ala Ala Thr Tyr Tyr Cys Gln Cys Thr Tyr Gly Ser Ser Ser
                 85                  90                  95

Ser Asn Ala Phe Gly Gly Gly Thr Lys Val Glu Ile Lys
                100                 105
```

<210> SEQ ID NO 28
<211> LENGTH: 119

<212> TYPE: PRT
<213> ORGANISM: Oryctolagus cuniculus

<400> SEQUENCE: 28

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Asn Tyr Asn
            20                  25                  30
Met Gly Trp Val Arg Gln Ala Pro Gly Glu Gly Leu Glu Tyr Ile Gly
        35                  40                  45
Ile Ile Ser Ser Gln Gly Asp Ile Tyr Tyr Ala Thr Trp Ala Lys Gly
50                  55                  60
Arg Phe Thr Ile Ser Lys Thr Ser Thr Thr Val Asp Leu Lys Ile Thr
65                  70                  75                  80
Ser Pro Thr Thr Glu Asp Thr Ala Thr Tyr Phe Cys Ala Arg Ala Arg
                85                  90                  95
His Val Gly Ser Ala Ala Asp Ser Tyr Phe His Leu Trp Gly Leu Gly
            100                 105                 110
Thr Leu Val Thr Val Ser Ser
            115
```

<210> SEQ ID NO 29
<211> LENGTH: 112
<212> TYPE: PRT
<213> ORGANISM: Oryctolagus cuniculus

<400> SEQUENCE: 29

```
Ala Val Val Leu Thr Gln Thr Ala Ser Pro Val Ser Ala Ala Val Gly
1               5                   10                  15
Gly Thr Val Thr Ile Asn Cys Gln Ala Ser Glu Glu Ile Tyr Arg Asn
            20                  25                  30
Leu Ala Trp Tyr Gln Gln Lys Pro Gly Gln Arg Pro Lys Leu Leu Ile
        35                  40                  45
Tyr Gly Ala Ser Asn Leu Ala Ser Gly Val Pro Ser Arg Phe Ser Gly
50                  55                  60
Ser Gly Ser Gly Thr Glu Tyr Thr Leu Thr Ile Ser Asp Leu Glu Cys
65                  70                  75                  80
Ala Asp Ala Ala Thr Tyr Tyr Cys Gln Arg Tyr Ala Trp Gly Lys Asn
                85                  90                  95
Ser Ala Asp Gly Asn Thr Phe Gly Gly Gly Thr Lys Val Glu Ile Lys
            100                 105                 110
```

<210> SEQ ID NO 30
<211> LENGTH: 113
<212> TYPE: PRT
<213> ORGANISM: Oryctolagus cuniculus

<400> SEQUENCE: 30

```
Gln Ser Val Glu Glu Ser Gly Gly Arg Leu Val Thr Pro Gly Thr Pro
1               5                   10                  15
Leu Thr Leu Thr Cys Thr Ala Ser Gly Phe Ser Leu Ser Ser Ala Tyr
            20                  25                  30
Met Asn Trp Val Arg Gln Ala Pro Gly Lys Gly Leu Glu Trp Ile Gly
        35                  40                  45
Ile Ile Tyr Ala Ser Gly Ser Thr Tyr Tyr Ala Ser Trp Ala Lys Gly
50                  55                  60
Arg Phe Thr Ile Ser Lys Thr Ser Thr Thr Val Asp Leu Lys Ile Thr
```

```
                65                  70                  75                  80
Ser Pro Thr Thr Glu Asp Thr Ala Thr Tyr Phe Cys Ala Arg Asp Asp
                    85                  90                  95

Tyr Gly Thr Ala Asp Leu Trp Gly Pro Gly Thr Leu Val Thr Val Ser
                100                 105                 110

Ser

<210> SEQ ID NO 31
<211> LENGTH: 112
<212> TYPE: PRT
<213> ORGANISM: Oryctolagus cuniculus

<400> SEQUENCE: 31

Ala Val Val Leu Thr Gln Thr Ala Ser Pro Val Ser Ala Pro Val Gly
1               5                   10                  15

Gly Thr Val Thr Ile Lys Cys Gln Ala Ser Gln Ser Ile Gly Ser Ser
                20                  25                  30

Leu Ala Trp Tyr Gln Gln Lys Pro Gly Gln Ser Pro Lys Leu Leu Ile
            35                  40                  45

Tyr Gly Ala Ser Thr Leu Val Ser Gly Val Ser Ser Arg Phe Ser Gly
        50                  55                  60

Ser Arg Ser Gly Thr Glu Phe Ser Leu Thr Ile Ser Asp Leu Glu Cys
65                  70                  75                  80

Ala Asp Ala Ala Thr Tyr Tyr Cys Gln Asn Tyr Tyr Leu Ser Ser Ser
                85                  90                  95

Ser Ala Asp Arg Arg Thr Phe Gly Gly Gly Thr Lys Val Glu Ile Lys
                100                 105                 110

<210> SEQ ID NO 32
<211> LENGTH: 5
<212> TYPE: PRT
<213> ORGANISM: Oryctolagus cuniculus

<400> SEQUENCE: 32

Ser Tyr Ala Met Ser
1               5

<210> SEQ ID NO 33
<211> LENGTH: 16
<212> TYPE: PRT
<213> ORGANISM: Oryctolagus cuniculus

<400> SEQUENCE: 33

Ile Ile Thr Asn Leu Asp Asn Thr Tyr Tyr Ala Asn Trp Ala Lys Gly
1               5                   10                  15

<210> SEQ ID NO 34
<211> LENGTH: 19
<212> TYPE: PRT
<213> ORGANISM: Oryctolagus cuniculus

<400> SEQUENCE: 34

Glu Arg Ile Lys Arg Lys Tyr Ser Tyr Asp Asp Tyr Gly Gly Trp Ala
1               5                   10                  15

Phe Asp Pro

<210> SEQ ID NO 35
<211> LENGTH: 11
<212> TYPE: PRT
<213> ORGANISM: Oryctolagus cuniculus
```

<400> SEQUENCE: 35

Gln Ala Ile Glu Asn Ile Tyr Arg Ser Leu Ala
1               5                   10

<210> SEQ ID NO 36
<211> LENGTH: 7
<212> TYPE: PRT
<213> ORGANISM: Oryctolagus cuniculus

<400> SEQUENCE: 36

Asp Thr Ser Asp Leu Ala Ser
1               5

<210> SEQ ID NO 37
<211> LENGTH: 12
<212> TYPE: PRT
<213> ORGANISM: Oryctolagus cuniculus

<400> SEQUENCE: 37

Gln Ser Tyr Tyr Tyr Ser Ser Val Thr Tyr Asn Ala
1               5                   10

<210> SEQ ID NO 38
<211> LENGTH: 5
<212> TYPE: PRT
<213> ORGANISM: Oryctolagus cuniculus

<400> SEQUENCE: 38

Asn Tyr Ala Ile His
1               5

<210> SEQ ID NO 39
<211> LENGTH: 17
<212> TYPE: PRT
<213> ORGANISM: Oryctolagus cuniculus

<400> SEQUENCE: 39

Tyr Ile Tyr Ala Arg Ser Gly Val Thr Trp Tyr Ala Ser Trp Val Lys
1               5                   10                  15

Gly

<210> SEQ ID NO 40
<211> LENGTH: 14
<212> TYPE: PRT
<213> ORGANISM: Oryctolagus cuniculus

<400> SEQUENCE: 40

Val Leu Ala Gly Gly Gly Tyr Ala Asn Thr Gly Leu Ser Leu
1               5                   10

<210> SEQ ID NO 41
<211> LENGTH: 11
<212> TYPE: PRT
<213> ORGANISM: Oryctolagus cuniculus

<400> SEQUENCE: 41

Gln Ala Ser Gln Asn Ile Gly Tyr Ser Ser Ala
1               5                   10

<210> SEQ ID NO 42
<211> LENGTH: 7
<212> TYPE: PRT
<213> ORGANISM: Oryctolagus cuniculus

<400> SEQUENCE: 42

Gly Ala Ser Thr Leu Ala Ser
1               5

<210> SEQ ID NO 43
<211> LENGTH: 13
<212> TYPE: PRT
<213> ORGANISM: Oryctolagus cuniculus

<400> SEQUENCE: 43

Gln Ser Asn Tyr Ile Ser Ser Gly Ser Val Asp Gly Thr
1               5                   10

<210> SEQ ID NO 44
<211> LENGTH: 5
<212> TYPE: PRT
<213> ORGANISM: Oryctolagus cuniculus

<400> SEQUENCE: 44

Ser Cys Tyr Met Ser
1               5

<210> SEQ ID NO 45
<211> LENGTH: 17
<212> TYPE: PRT
<213> ORGANISM: Oryctolagus cuniculus

<400> SEQUENCE: 45

Thr Ile Tyr Thr Gly Ser Gly Ala Thr Tyr Tyr Ala Ser Trp Ala Lys
1               5                   10                  15

Gly

<210> SEQ ID NO 46
<211> LENGTH: 16
<212> TYPE: PRT
<213> ORGANISM: Oryctolagus cuniculus

<400> SEQUENCE: 46

Ala Ile Tyr Pro Gly Ser Ser Ser Asn Leu Cys Ala Phe Asp Leu
1               5                   10                  15

<210> SEQ ID NO 47
<211> LENGTH: 13
<212> TYPE: PRT
<213> ORGANISM: Oryctolagus cuniculus

<400> SEQUENCE: 47

Gln Ala Ser Gln Ser Val Tyr Asp Asn Asn Trp Leu Ala
1               5                   10

<210> SEQ ID NO 48
<211> LENGTH: 7
<212> TYPE: PRT
<213> ORGANISM: Oryctolagus cuniculus

<400> SEQUENCE: 48

Gln Ala Ser Ser Leu Ala Ser
1               5

<210> SEQ ID NO 49
<211> LENGTH: 10
<212> TYPE: PRT
<213> ORGANISM: Oryctolagus cuniculus

```
<400> SEQUENCE: 49

Gln Gly Tyr Tyr Ala Gly Val Leu Tyr Ser
1               5                   10

<210> SEQ ID NO 50
<211> LENGTH: 5
<212> TYPE: PRT
<213> ORGANISM: Oryctolagus cuniculus

<400> SEQUENCE: 50

Asn Tyr Tyr Met Thr
1               5

<210> SEQ ID NO 51
<211> LENGTH: 16
<212> TYPE: PRT
<213> ORGANISM: Oryctolagus cuniculus

<400> SEQUENCE: 51

Ile Ile Asn Thr Asp Gly Gly Thr Tyr Tyr Ala Ser Trp Ala Lys Gly
1               5                   10                  15

<210> SEQ ID NO 52
<211> LENGTH: 14
<212> TYPE: PRT
<213> ORGANISM: Oryctolagus cuniculus

<400> SEQUENCE: 52

Gly Val Phe Thr Gly Gly Trp Thr Gly Met Arg Thr Asn Leu
1               5                   10

<210> SEQ ID NO 53
<211> LENGTH: 11
<212> TYPE: PRT
<213> ORGANISM: Oryctolagus cuniculus

<400> SEQUENCE: 53

Gln Ala Ser Glu Asp Ile Tyr Ile Leu Leu Ala
1               5                   10

<210> SEQ ID NO 54
<211> LENGTH: 7
<212> TYPE: PRT
<213> ORGANISM: Oryctolagus cuniculus

<400> SEQUENCE: 54

Ala Ala Ser Asn Leu Glu Ser
1               5

<210> SEQ ID NO 55
<211> LENGTH: 11
<212> TYPE: PRT
<213> ORGANISM: Oryctolagus cuniculus

<400> SEQUENCE: 55

Gln Cys Thr Tyr Gly Ser Ser Ser Asn Ala
1               5                   10

<210> SEQ ID NO 56
<211> LENGTH: 5
<212> TYPE: PRT
<213> ORGANISM: Oryctolagus cuniculus

<400> SEQUENCE: 56
```

```
Asn Tyr Asn Met Gly
1               5

<210> SEQ ID NO 57
<211> LENGTH: 16
<212> TYPE: PRT
<213> ORGANISM: Oryctolagus cuniculus

<400> SEQUENCE: 57

Ile Ile Ser Ser Gln Gly Asp Ile Tyr Tyr Ala Thr Trp Ala Lys Gly
1               5                   10                  15

<210> SEQ ID NO 58
<211> LENGTH: 14
<212> TYPE: PRT
<213> ORGANISM: Oryctolagus cuniculus

<400> SEQUENCE: 58

Ala Arg His Val Gly Ser Ala Ala Asp Ser Tyr Phe His Leu
1               5                   10

<210> SEQ ID NO 59
<211> LENGTH: 11
<212> TYPE: PRT
<213> ORGANISM: Oryctolagus cuniculus

<400> SEQUENCE: 59

Gln Ala Ser Glu Glu Ile Tyr Arg Asn Leu Ala
1               5                   10

<210> SEQ ID NO 60
<211> LENGTH: 7
<212> TYPE: PRT
<213> ORGANISM: Oryctolagus cuniculus

<400> SEQUENCE: 60

Gly Ala Ser Asn Leu Ala Ser
1               5

<210> SEQ ID NO 61
<211> LENGTH: 14
<212> TYPE: PRT
<213> ORGANISM: Oryctolagus cuniculus

<400> SEQUENCE: 61

Gln Arg Tyr Ala Trp Gly Lys Asn Ser Ala Asp Gly Asn Thr
1               5                   10

<210> SEQ ID NO 62
<211> LENGTH: 5
<212> TYPE: PRT
<213> ORGANISM: Oryctolagus cuniculus

<400> SEQUENCE: 62

Ser Ala Tyr Met Asn
1               5

<210> SEQ ID NO 63
<211> LENGTH: 16
<212> TYPE: PRT
<213> ORGANISM: Oryctolagus cuniculus

<400> SEQUENCE: 63

Ile Ile Tyr Ala Ser Gly Ser Thr Trp Tyr Ala Ser Trp Ala Lys Gly
1               5                   10                  15
```

```
<210> SEQ ID NO 64
<211> LENGTH: 8
<212> TYPE: PRT
<213> ORGANISM: Oryctolagus cuniculus

<400> SEQUENCE: 64

Asp Asp Tyr Gly Thr Ala Asp Leu
1               5

<210> SEQ ID NO 65
<211> LENGTH: 11
<212> TYPE: PRT
<213> ORGANISM: Oryctolagus cuniculus

<400> SEQUENCE: 65

Gln Ala Ser Gln Ser Ile Gly Ser Ser Leu Ala
1               5                   10

<210> SEQ ID NO 66
<211> LENGTH: 7
<212> TYPE: PRT
<213> ORGANISM: Oryctolagus cuniculus

<400> SEQUENCE: 66

Gly Ala Ser Thr Leu Val Ser
1               5

<210> SEQ ID NO 67
<211> LENGTH: 14
<212> TYPE: PRT
<213> ORGANISM: Oryctolagus cuniculus

<400> SEQUENCE: 67

Gln Asn Tyr Tyr Leu Ser Ser Ser Ser Ala Asp Arg Arg Thr
1               5                   10

<210> SEQ ID NO 68
<211> LENGTH: 112
<212> TYPE: PRT
<213> ORGANISM: Artificial
<220> FEATURE:
<223> OTHER INFORMATION: an artificially synthesized sequence

<400> SEQUENCE: 68

Ala Val Val Leu Thr Gln Thr Ala Ser Pro Val Ser Ala Ala Val Gly
1               5                   10                  15

Gly Thr Val Thr Ile Asn Cys Gln Ala Ser Glu Glu Ile Tyr Arg Asn
                20                  25                  30

Leu Ala Trp Tyr Gln Gln Lys Pro Gly Gln Arg Pro Lys Leu Leu Ile
            35                  40                  45

Tyr Gly Ala Ser Asn Leu Ala Ser Gly Val Pro Ser Arg Phe Ser Gly
        50                  55                  60

Ser Gly Ser Gly Thr Glu Tyr Thr Leu Thr Ile Ser Asp Leu Glu Ser
65                  70                  75                  80

Ala Asp Ala Ala Thr Tyr Tyr Cys Gln Arg Tyr Ala Trp Gly Lys Asn
                85                  90                  95

Ser Ala Asp Gly Asn Thr Phe Gly Gly Gly Thr Lys Val Glu Ile Lys
            100                 105                 110

<210> SEQ ID NO 69
```

<211> LENGTH: 324
<212> TYPE: PRT
<213> ORGANISM: Artificial
<220> FEATURE:
<223> OTHER INFORMATION: an artificially synthesized sequence

<400> SEQUENCE: 69

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 70
<211> LENGTH: 107
<212> TYPE: PRT
<213> ORGANISM: Mus musculus

<400> SEQUENCE: 70

Arg Ala Asp Ala Ala Pro Thr Val Ser Ile Phe Pro Pro Ser Ser Glu

```
1               5                   10                  15
Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```

ANTI-MASP-1 ANTIBODIES AND METHODS OF USE

CROSS-REFERENCE TO RELATED APPLICATIONS

This application is a U.S. National Phase of PCT Application No. PCT/JP2018/014046, filed Apr. 2, 2018, which claims the benefit of Japanese Patent Application No. 2017-073428, filed Apr. 3, 2017, each of which is incorporated herein by reference in its entirety.

REFERENCE TO SEQUENCE LISTING SUBMITTED ELECTRONICALLY

The content of the electronically submitted sequence listing (Name: 6663_0122_Sequence_Listing.txt; Size: 92.8 kilobytes; and Date of Creation: Oct. 2, 2019) filed with the application is incorporated herein by reference in its entirety.

TECHNICAL FIELD

The present invention relates to anti-MASP-1 antibodies and methods of using the same.

BACKGROUND ART

The complement system plays a crucial role in the innate immune response (NPL 1). It is widely accepted that the complement system can be activated through three distinct pathways: the classical pathway (CP), lectin pathway (LP), and alternative pathway (AP). Activation of these pathways leads to a number of immunological effector functions including recruitment of inflammatory cells, augmentation of phagocytosis, and formation of membrane attack complex (MAC) on the surface of the target cell.

The first step of the LP is the binding of pattern-recognition molecules (PRMs), such as mannan-binding lectin (MBL), collectin-10, collectin-11, and the ficolins (ficolin-1, ficolin-2, and ficolin-3), to patterns of ligands, e.g., surface-linked carbohydrates or acetyl groups on pathogens or damaged self-tissue (NPL 2). The PRMs are subsequently associated with three MBL-associated serine proteases (MASP-1, MASP-2, and MASP-3). MASP-2 was originally considered to auto activate and be the only active protease in the LP. However, many recent reports show that MASP-1 activates MASP-2 and is essential for the LP. When PRM-MASP complexes bind to target cells, MASP-1 will first autoactivate and then it activates MASP-2 and MASP-3. The activated MASP-2 cleaves C4 into C4a, C4b, and C4c, while activated MASP-1 and MASP-2 cleave C2 into C2a and C2b. The assembly of the C4a and C2b fragments results in the formation of the C3 convertase C4bC2a, to subsequently activate the complement system. In addition to its complement activating property, MASP-1 mediates coagulation and also contributes to a more powerful inflammatory reaction through bradykinin release, and endothelial and platelet activation (NPL 3).

While a properly functioning LP provides a robust defense against infectious microbes and maintenance of tissue homeostasis, inappropriate regulation of the LP has been implicated in the pathogenesis of a variety of disorders including, e.g., thrombosis (NPL 4); IgA nephropathy (NPL 5); and delayed graft function in transplanted kidneys (NPL 6). Therefore, MASP-1 inhibitory agents would serve effective therapeutic options in the treatment of diseases caused by the LP activation.

MASP-1 and MASP-3 are the alternative splicing variants of the MASP-1 gene. They contain five identical domains (CUB1-EGF-CUB2-CCP1-CCP2) prolonged by different serine protease domains at the C-terminal end. Mutations in MASP-1 gene were found to be responsible for 3MC syndrome, which is characterized by hearing loss and distinctive facial features including hypertelorism, blepharophimosis, and highly arched eyebrows. The disruption of MASP-3 with normal MASP-1 was found to be sufficient to cause 3MC syndrome (NPL 7). Thus, there is a need to develop therapeutically effective MASP-1 specific inhibitors to provide robust efficacy and to prevent adverse effects for patients with thrombosis and other lectin pathway-mediated disorders.

CITATION LIST

Non Patent Literature

[NPL 1] Holers, V. M., Annual review of immunology 32, 433-459, 2014
[NPL 2] Jozsef, D, et. al, Immunological Reviews 274, 98-111, 2016
[NPL 3] Peter G, et. al., Immunological Reviews 274, 74-97, 2016
[NPL 4] La Bonte L. R., et. al., J. Immunol., 188, 885-891, 2012
[NPL 5] Liu L. L., et. al., Clinical & Experimental Immunology, 174, 152-160, 2013
[NPL 6] Giuseppe C, et. al., American Journal of Pathology, 176 (4), 1648-1659, 2010
[NPL 7] Tahir A, et. al., Orphanet Journal of Rare Diseases, 10, 128, 2015

SUMMARY OF INVENTION

Technical Problem

An objective of the invention is to provide anti-MASP-1 antibodies and methods of using the same.

Solution to Problem

The invention provides anti-MASP-1 antibodies and methods of using the same.

In some embodiments, an anti-MASP-1 antibody of the present invention specifically binds to MASP-1. In some embodiments, an anti-MASP-1 antibody of the present invention binds to MASP-1 but does not or does not substantially bind to MASP-3. In further embodiments, an anti-MASP-1 antibody of the present invention binds to the serine protease domain of MASP-1.

In some embodiments, an anti-MASP-1 antibody of the present invention inhibits activity of MASP-1. In some embodiments, an anti-MASP-1 antibody of the present invention does not inhibit activity of MASP-3. In certain embodiments, the activity of MASP-1 is complement lectin-pathway activation mediated by MASP-1, and the activity MASP-3 is complement lectin-pathway activation mediated by MASP-3.

In some embodiments, an anti-MASP-1 antibody of the present invention is selected from the group consisting of:
  (a) an antibody comprising the HVR-H1 sequence of SEQ ID NO: 32, the HVR-H2 sequence of SEQ ID NO: 33, the HVR-H3 sequence of SEQ ID NO: 34, the HVR-L1 sequence of SEQ ID NO: 35, the HVR-L2 sequence of SEQ ID NO: 36, and the HVR-L3 sequence of SEQ ID NO: 37;
(b) an antibody comprising the HVR-H1 sequence of SEQ ID NO: 38, the HVR-H2 sequence of SEQ ID NO: 39, the HVR-H3 sequence of SEQ ID NO: 40, the HVR-L1 sequence of SEQ ID NO: 41, the HVR-L2 sequence of SEQ ID NO: 42, and the HVR-L3 sequence of SEQ ID NO: 43;
(c) an antibody comprising the HVR-H1 sequence of SEQ ID NO: 44, the HVR-H2 sequence of SEQ ID NO: 45, the HVR-H3 sequence of SEQ ID NO: 46, the HVR-L1 sequence of SEQ ID NO: 47, the HVR-L2 sequence of SEQ ID NO: 48, and the HVR-L3 sequence of SEQ ID NO: 49;
(d) an antibody comprising the HVR-H1 sequence of SEQ ID NO: 50, the HVR-H2 sequence of SEQ ID NO: 51, the HVR-H3 sequence of SEQ ID NO: 52, the HVR-L1 sequence of SEQ ID NO: 53, the HVR-L2 sequence of SEQ ID NO: 54, and the HVR-L3 sequence of SEQ ID NO: 55;
(e) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 59, the HVR-L2 sequence of SEQ ID NO: 60, and the HVR-L3 sequence of SEQ ID NO: 61; and
(f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 65, the HVR-L2 sequence of SEQ ID NO: 66, and the HVR-L3 sequence of SEQ ID NO: 67.

In some embodiments, an anti-MASP-1 antibody of the present invention binds to the same epitope as a reference antibody which is selected from the group consisting of:
(a) an antibody comprising the HVR-H1 sequence of SEQ ID NO: 32, the HVR-H2 sequence of SEQ ID NO: 33, the HVR-H3 sequence of SEQ ID NO: 34, the HVR-L1 sequence of SEQ ID NO: 35, the HVR-L2 sequence of SEQ ID NO: 36, and the HVR-L3 sequence of SEQ ID NO: 37;
(b) an antibody comprising the HVR-H1 sequence of SEQ ID NO: 38, the HVR-H2 sequence of SEQ ID NO: 39, the HVR-H3 sequence of SEQ ID NO: 40, the HVR-L1 sequence of SEQ ID NO: 41, the HVR-L2 sequence of SEQ ID NO: 42, and the HVR-L3 sequence of SEQ ID NO: 43;
(c) an antibody comprising the HVR-H1 sequence of SEQ ID NO: 44, the HVR-H2 sequence of SEQ ID NO: 45, the HVR-H3 sequence of SEQ ID NO: 46, the HVR-L1 sequence of SEQ ID NO: 47, the HVR-L2 sequence of SEQ ID NO: 48, and the HVR-L3 sequence of SEQ ID NO: 49;
(d) an antibody comprising the HVR-H1 sequence of SEQ ID NO: 50, the HVR-H2 sequence of SEQ ID NO: 51, the HVR-H3 sequence of SEQ ID NO: 52, the HVR-L1 sequence of SEQ ID NO: 53, the HVR-L2 sequence of SEQ ID NO: 54, and the HVR-L3 sequence of SEQ ID NO: 55;
(e) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 59, the HVR-L2 sequence of SEQ ID NO: 60, and the HVR-L3 sequence of SEQ ID NO: 61; and
(f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 65, the HVR-L2 sequence of SEQ ID NO: 66, and the HVR-L3 sequence of SEQ ID NO: 67.

In some embodiments, an anti-MASP-1 antibody of the present invention is capable of binding to, and inhibiting activity of, human MASP-1, cynomolgus monkey MASP-1, and/or mouse MASP-1.

In some embodiments, an anti-MASP-1 antibody of the present invention inhibits C3 and/or C4 activation with an IC 50 of less than 0.35 micro g/mL.

In some embodiments, an anti-MASP-1 antibody of the present invention is a monoclonal antibody. In further embodiments, an anti-MASP-1 antibody of the present invention is a human, humanized, or chimeric antibody. In certain embodiments, an anti-MASP-1 antibody of the present invention is an antibody fragment that binds to MASP-1.

The invention also provides nucleic acids comprising a nucleotide sequence encoding an anti-MASP-1 antibody of the present invention. The invention also provides recombinant vectors comprising a nucleic acid of the present invention. The invention also provides recombinant cells comprising a nucleic acid or a recombinant vector of the present invention. The invention also provides methods of producing an antibody comprising culturing a recombinant cell of the present invention so that the antibody is produced.

The invention also provides pharmaceutical compositions comprising an anti-MASP-1 antibody of the present invention and a pharmaceutically acceptable carrier.

Anti-MASP-1 antibodies of the present invention may be for use as a medicament. Anti-MASP-1 antibodies of the present invention may be for use in treating a disease caused by complement lectin-pathway activation. In certain embodiments, the disease caused by the complement lectin-pathway activation is thrombotic microangiopathy (TMA). In certain embodiments, the subject is a human.

In some embodiments, anti-MASP-1 antibodies of the present invention may be for use in inhibiting complement lectin-pathway activation mediated by MASP-1. In some embodiments, anti-MASP-1 antibodies of the present invention may be for use in inhibiting C3 and/or C4 activation.

The invention also provides methods of treating a subject having a disease caused by complement lectin-pathway activation. In some embodiments, a method of the present invention comprises administering to the subject an effective amount of an antibody of the present invention. In certain embodiments, the disease caused by the complement lectin-pathway activation is thrombotic microangiopathy (TMA). In certain embodiments, the subject is a human.

The invention also provides methods of inhibiting complement lectin-pathway activation mediated by MASP-1 in a subject. In some embodiments, a method of the present invention comprises administering to the subject an effective amount of an antibody of the present invention. The invention also provides methods of inhibiting C3 and/or C4 activation in a subject. In some embodiments, a method of the present invention comprises administering to the subject an effective amount of an antibody of the present invention.

Anti-MASP-1 antibodies of the present invention may be used in the manufacture of a medicament. In some embodiments, the medicament is for treating a disease caused by complement lectin-pathway activation. In certain embodiments, the disease caused by complement lectin-pathway activation is thrombotic microangiopathy (TMA).

The invention also provides methods of inhibiting C3 and/or C4 activation in serum. In some embodiments, a method of the present invention comprises contacting an antibody of the present invention with mannan and a biological sample containing MBL (mannose-binding lectin), MASP-1, C2 and C4 under conditions permissive for binding of the antibody to MASP-1. In some embodiments, the biological sample is a human serum, cynomolgus monkey serum, or mouse serum.

The invention also provides methods of detecting the presence of MASP-1. In some embodiments, a method of the present invention comprises:
  (a) contacting a biological sample with an antibody of the present invention under conditions permissive for binding of the antibody to MASP-1; and
  (b) detecting whether a complex is formed between the antibody and MASP-1.

The invention also provides methods for producing an anti-MASP-1 antibody which inhibits MASP-1 activity but does not inhibit MASP-3 activity. In some embodiments, an method of the present invention comprises:
  (a) (i) contacting a biological sample comprising mannan and serum with a test antibody, wherein the serum contains MASP-1 but does not contain MASP-3, and (ii) measuring inhibition of C3 and/or C4 activation;
  (b) (i) contacting a biological sample comprising mannan and serum with a test antibody, wherein the serum contains MASP-3 but does not contain MASP-1, and (ii) measuring inhibition of C3 and/or C4 activation;
  (c) selecting the test antibody which inhibits MASP-1 activity but does not inhibit MASP-3 activity, if the test antibody inhibits C3 and/or C4 activation in step (a) but does not inhibit C3 and/or C4 activation in step (b);
  (d) obtaining amino acid sequence information of the anti-MASP-1 antibody selected in step (c); and
  (e) introducing a gene encoding the amino acid sequence obtained in step (d) into a host cell.

More specifically, the present invention provides the following:
  [1] An anti-MASP-1 antibody which specifically binds to MASP-1.
  [2] An anti-MASP-1 antibody which binds to MASP-1 but does not bind to MASP-3.
  [3] An anti-MASP-1 antibody which binds to the serine protease domain of MASP-1.
  [4] The anti-MASP-1 antibody according to any one of [1] to [3], wherein the antibody inhibits MASP-1 activity.
  [5] The anti-MASP-1 antibody according to any one of [1] to [4], wherein the antibody does not inhibit MASP-3 activity.
  [6] The anti-MASP-1 antibody according to [5], wherein the MASP-1 activity is MASP-1 mediated complement lectin-pathway activation and the MASP-3 activity is MASP-3 mediated complement lectin-pathway activation.
  [7] The anti-MASP-1 antibody according to any one of [1] to [6], wherein the antibody competes for binding to MASP-1 with an antibody selected from the group consisting of:
    (a) an antibody comprising the HVR-H1 sequence of SEQ ID NO: 32, the HVR-H2 sequence of SEQ ID NO: 33, the HVR-H3 sequence of SEQ ID NO: 34, the HVR-L1 sequence of SEQ ID NO: 35, the HVR-L2 sequence of SEQ ID NO: 36, and the HVR-L3 sequence of SEQ ID NO: 37;
    (b) an antibody comprising the HVR-H1 sequence of SEQ ID NO: 38, the HVR-H2 sequence of SEQ ID NO: 39, the HVR-H3 sequence of SEQ ID NO: 40, the HVR-L1 sequence of SEQ ID NO: 41, the HVR-L2 sequence of SEQ ID NO: 42, and the HVR-L3 sequence of SEQ ID NO: 43;
    (c) an antibody comprising the HVR-H1 sequence of SEQ ID NO: 44, the HVR-H2 sequence of SEQ ID NO: 45, the HVR-H3 sequence of SEQ ID NO: 46, the HVR-L1 sequence of SEQ ID NO: 47, the HVR-L2 sequence of SEQ ID NO: 48, and the HVR-L3 sequence of SEQ ID NO: 49;
    (d) an antibody comprising the HVR-H1 sequence of SEQ ID NO: 50, the HVR-H2 sequence of SEQ ID NO: 51, the HVR-H3 sequence of SEQ ID NO: 52, the HVR-L1 sequence of SEQ ID NO: 53, the HVR-L2 sequence of SEQ ID NO: 54, and the HVR-L3 sequence of SEQ ID NO: 55;
    (e) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 59, the HVR-L2 sequence of SEQ ID NO: 60, and the HVR-L3 sequence of SEQ ID NO: 61; and
    (f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 65, the HVR-L2 sequence of SEQ ID NO: 66, and the HVR-L3 sequence of SEQ ID NO: 67.
  [8] The anti-MASP-1 antibody according to any one of [1] to [7], wherein the antibody binds to the same epitope to which a reference antibody binds, wherein the reference antibody is selected from the group consisting of:
    (a) an antibody comprising the HVR-H1 sequence of SEQ ID NO: 32, the HVR-H2 sequence of SEQ ID NO: 33, the HVR-H3 sequence of SEQ ID NO: 34, the HVR-L1 sequence of SEQ ID NO: 35, the HVR-L2 sequence of SEQ ID NO: 36, and the HVR-L3 sequence of SEQ ID NO: 37;
    (b) an antibody comprising the HVR-H1 sequence of SEQ ID NO: 38, the HVR-H2 sequence of SEQ ID NO: 39, the HVR-H3 sequence of SEQ ID NO: 40, the HVR-L1 sequence of SEQ ID NO: 41, the HVR-L2 sequence of SEQ ID NO: 42, and the HVR-L3 sequence of SEQ ID NO: 43;
    (c) an antibody comprising the HVR-H1 sequence of SEQ ID NO: 44, the HVR-H2 sequence of SEQ ID NO: 45, the HVR-H3 sequence of SEQ ID NO: 46, the HVR-L1 sequence of SEQ ID NO: 47, the HVR-L2 sequence of SEQ ID NO: 48, and the HVR-L3 sequence of SEQ ID NO: 49;
    (d) an antibody comprising the HVR-H1 sequence of SEQ ID NO: 50, the HVR-H2 sequence of SEQ ID NO: 51, the HVR-H3 sequence of SEQ ID NO: 52, the HVR-L1 sequence of SEQ ID NO: 53, the HVR-L2 sequence of SEQ ID NO: 54, and the HVR-L3 sequence of SEQ ID NO: 55;
    (e) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 59, the HVR-L2 sequence of SEQ ID NO: 60, and the HVR-L3 sequence of SEQ ID NO: 61; and
    (f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 65, the HVR-L2 sequence of SEQ ID NO: 66, and the HVR-L3 sequence of SEQ ID NO: 67.

[9] The anti-MASP-1 antibody according to any one of [1] to [8], wherein the antibody is capable of binding to, and inhibiting activity of, human MASP-1, cynomolgus monkey MASP-1, and/or mouse MASP-1.

[10] The anti-MASP-1 antibody according to any one of [1] to [9], wherein the antibody inhibits C3 and/or C4 activation with an IC 50 of less than 0.35 micro g/mL.

[11] The anti-MASP-1 antibody according to any one of [1] to [10], wherein the antibody is a monoclonal antibody.

[12] The anti-MASP-1 antibody according to any one of [1] to [11], wherein the antibody is a human, humanized or chimeric antibody.

[13] The anti-MASP-1 antibody according to any one of [1] to [11], wherein the antibody is an antibody fragment that binds to MASP-1.

[14] A nucleic acid comprising a nucleotide sequence encoding the antibody of any one of [1] to [13].

[15] A recombinant vector comprising the nucleic acid of [14].

[16] A recombinant cell comprising the nucleic acid of [14] or the recombinant vector of [15].

[17] A method of producing an antibody comprising culturing the recombinant cell of [16] so that the antibody is produced.

[18] A pharmaceutical composition comprising the antibody according to any one of [1] to [13] and a pharmaceutically acceptable carrier.

[19] A pharmaceutical composition for use in treating a disease caused by the complement lectin-pathway activation in a subject comprising the antibody according to any one of [1] to [13].

[20] The pharmaceutical composition according to [19], wherein the disease caused by the complement lectin-pathway activation is TMA.

[21] The pharmaceutical composition according to [19] or [20], wherein the subject is a human.

[22] The antibody according to any one of [1] to [13] for use in a method of treating TMA.

[23] A method of treating a subject having a disease caused by the complement lectin-pathway activation comprising administering to the subject an effective amount of the antibody according to any one of [1] to [13].

[24] The method according to [23], wherein the disease caused by the complement lectin-pathway activation is TMA.

[25] The method according to [23] or [24], wherein the subject is a human.

[26] Use of the antibody according to any one of [1] to [13] in the manufacture of a medicament of treating a disease caused by the complement lectin-pathway activation.

[27] The use according to [26], wherein the disease caused by the complement lectin-pathway activation is TMA.

[28] A method of inhibiting C3 and/or C4 activation in serum, comprising contacting the antibody according to any one of [1] to [13] with mannan and a biological sample containing MBL (mannan-binding lectin), MASP-1, C2 and C4 under conditions permissive for binding of the antibody to MASP-1.

[29] The method according to [28], wherein the biological sample is human serum, cynomolgus monkey serum or mouse serum.

[30] A method of detecting the presence of MASP-1 comprising:
(a) contacting a biological sample with the antibody according to any one of [1] to [13] under conditions permissive for binding of the antibody to MASP-1; and
(b) detecting whether a complex is formed between the antibody and MASP-1.

[31] A method for producing an anti-MASP-1 antibody which inhibits MASP-1 activity but does not inhibit MASP-3 activity, comprising:
(a) (i) contacting a biological sample comprising mannan and serum with a test antibody, wherein the serum contains MASP-1 but does not contain MASP-3, and
(ii) measuring inhibition of C3 and/or C4 activation;
(b) (i) contacting a biological sample comprising mannan and serum with a test antibody, wherein the serum contains MASP-3 but does not contain MASP-1, and
(ii) measuring inhibition of C3 and/or C4 activation;
(c) selecting the test antibody which inhibits MASP-1 activity but does not inhibit MASP-3 activity, if the test antibody inhibits C3 and/or C4 activation in step (a) but does not inhibit C3 and/or C4 activation in step (b);
(d) obtaining amino acid sequence information of the anti-MASP-1 antibody selected in step (c); and
(e) introducing a gene encoding the amino acid sequence obtained in step (d) into a host cell.

[32] A pharmaceutical composition for use in inhibiting complement lectin-pathway activation mediated by MASP-1, comprising the antibody according to any one of [1] to [13].

[33] A pharmaceutical composition for use in inhibiting C3 and/or C4 activation, comprising the antibody according to any one of [1] to [13].

[34] A method of inhibiting complement lectin-pathway activation mediated by MASP-1 in a subject, comprising administering to the subject an effective amount of the antibody according to any one of [1] to [13].

[35] A method of inhibiting C3 and/or C4 activation in a subject, comprising administering to the subject an effective amount of the antibody according to any one of [1] to [13].

BRIEF DESCRIPTION OF DRAWINGS

FIG. 1 shows comparison of the amino acid sequences of the SP domain of human MASP-1 (SEQ ID NO: 7) and the SP domain of human MASP-3 (SEQ ID NO: 11).

FIG. 2 shows comparison of the amino acid sequences of the SP domains of human MASP-1 (SEQ ID NO: 7), monkey MASP-1 (SEQ ID NO: 8) and mouse MASP-1 (SEQ ID NO: 9).

FIGS. 3A-3C shows inhibition of C3c or C4c deposition by anti-MASP-1 monoclonal antibodies. FIG. 3A shows data indicating that anti-MASP-1 mAbs: MAS0102dd, MAS0114bb, MAS0116aa, MAS0154dd, and MAS0177hh, inhibited human C4c deposition. Similarly, these antibodies inhibited cynomolgus monkey C3c deposition (FIG. 3B). All of the antibodies except MAS0116aa inhibited mouse C4c deposition as well (FIG. 3C FIG. 4 shows the result of cynomolgus monkey C3c deposition assay using an anti-MASP-1 chimeric mAb (MAS0141aa) after 2-week incubation in PBS at 40 degrees C.

DESCRIPTION OF EMBODIMENTS

I. Definitions

Figure 4:
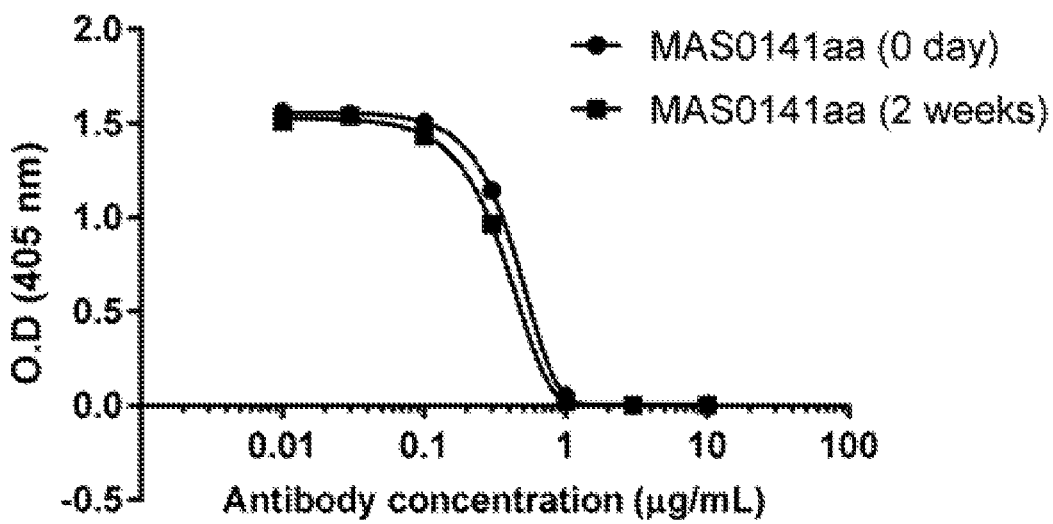

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-MASP-1 antibody" and "an antibody that binds to MASP-1" refer to an antibody that is capable of binding MASP-1 with sufficient affinity such that the antibody is useful as a diagnostic and/or therapeutic agent in targeting MASP-1. In one embodiment, the extent of binding of an anti-MASP-1 antibody to an unrelated, non-MASP-1 protein is less than about 10% of the binding of the antibody to MASP-1 as measured, e.g., by a radioimmunoassay (RIA). In certain embodiments, an antibody that binds to MASP-1 has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$M to $10^{-13}$M, e.g., from $10^{-9}$M to $10^{-13}$ M). In certain embodiments, an anti-MASP-1 antibody binds to an epitope of MASP-1 that is conserved among MASP-1 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Without intending to be bound by any theory, an antibody binds to its antigen with amino acids in more than one HVR.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

A "blocking" antibody or an "antagonist" antibody is one which significantly inhibits (either partially or completely) a biological activity of the antigen it binds.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called alpha, delta, epsilon, gamma, and mu, respectively.

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The term "Fc region-comprising antibody" refers to an antibody that comprises an Fc region. The C-terminal lysine (residue 447 according to the EU numbering system) or C-terminal glycine-lysine (residues 446-447) of the Fc region may be removed, for example, during purification of the antibody or by recombinant engineering of the nucleic acid encoding the antibody. Accordingly, a composition comprising an antibody having an Fc region according to this invention can comprise an antibody with G446-K447, with G446 and without K447, with all G446-K447 removed, or a mixture of three types of antibodies described above.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified in the heavy chain variable regions or light chain variable regions provided in Table 6.

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-MASP-1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa and lambda, based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The phrase "substantially reduced," "substantially inhibit" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values).

The term "substantially similar" or "substantially the same," as used herein, refers to a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values).

The term "MASP-1," as used herein, refers to any native MASP-1 from any vertebrate source, including mammals such as primates (e.g. humans) and rodents (e.g., mice and rats), unless otherwise indicated. The term encompasses "full-length" unprocessed MASP-1 as well as any form of MASP-1 that results from processing in the cell. The term also encompasses naturally occurring variants of MASP-1, e.g., splice variants or allelic variants. The amino acid sequence of an exemplary human MASP-1 is shown in SEQ ID NO: 1, and the nucleotide sequence encoding the exemplary human MASP-1 is shown in SEQ ID NO: 2. The amino acid sequences of an exemplary monkey MASP-1 and mouse MASP-1 are shown in SEQ ID NO: 3 and 4, respectively.

Accession numbers for exemplary MASP-1 are as follows:
Human MASP-1 protein: NCBI RefSeq NP_001870
Human MASP-1 nucleotide: NCBI RefSeq NM_001879
Mouse MASP-1 protein: NCBI RefSeq NP_032581
Mouse MASP-1 nucleotide: NCBI RefSeq NM_008555

The term "MASP-3," as used herein, refers to any native MASP-3 from any vertebrate source, including mammals such as primates (e.g. humans) and rodents (e.g., mice and rats), unless otherwise indicated. The term encompasses "full-length" unprocessed MASP-3 as well as any form of MASP-3 that results from processing in the cell. The term also encompasses naturally occurring variants of MASP-3, e.g., splice variants or allelic variants. The amino acid sequence of an exemplary human MASP-3 is shown in SEQ ID NO: 5.

NCBI RefSeq accession numbers for exemplary MASP-3 are as follows:
Human MASP-3 protein: Genbank AAK84071.1
Human MASP-3 nucleotide: GenBank AF284421.1
Monkey MASP-3 protein: GenBank AA106947
Mouse MASP-3 protein: GenBank BAB69688

MASP-1 and MASP-3 are alternative splicing variants of the MASP-3 gene. MASP-1 and MASP-3 have an identical heavy/alpha chain comprising, from the N-terminus, CUB1 (C1r/s, Uegf, Bone morphogenetic protein 1), EGF (epidermal growth factor), CUB2 (C1r/s, Uegf, Bone morphogenetic protein 2), CCP1 (complement control protein 1) and CCP2 (complement control protein 2). MASP-1 and MASP-3 have a different light/beta chain at the C-terminal end that comprises the SP (serine protease) domain containing a cleavage site that separates the heavy and light chain upon MASP activation.

For MASP-1, amino acid residues 1 to 19 of SEQ ID NO: 1 constitute a signal peptide. The amino acid sequence of the heavy/alpha chain of an exemplary human MASP-1 is SEQ ID NO: 6, which corresponds to amino acid residues 20 to 448 of SEQ ID NO: 1. The amino acid sequences of the CUB1 domain, EGF domain, CUB2 domain, CCP1 domain and CCP2 domain of an exemplary human MASP-1 are amino acid residues 20 to 138, 139 to 182, 185 to 297, 299 to 364, and 365 to 434 of SEQ ID NO: 1, respectively. The amino acid sequence of the SP domain of an exemplary human MASP-1 is SEQ ID NO: 7, which corresponds to amino acid residues 449 to 699 of SEQ ID NO: 1. The amino acid sequence of the SP domain of an exemplary monkey MASP-1 is SEQ ID NO: 8, which corresponds to amino acid residues 449 to 699 of SEQ ID NO: 3. The amino acid sequence of the SP domain of an exemplary mouse MASP-1 is SEQ ID NO: 9, which corresponds to amino acid residues 454 to 704 of SEQ ID NO: 4.

For MASP-3, the amino acid sequence of the heavy/alpha chain of an exemplary human MASP-3 is SEQ ID NO: 10, which corresponds to amino acid residues 20 to 449 of SEQ ID NO: 5. For MASP-3, amino acid residues 1 to 19 of SEQ ID NO: 5 constitute a signal peptide. The amino acid sequences of the CUB1 domain, EGF domain, CUB2 domain, CCP1 domain and CCP2 domain of an exemplary human MASP-3 are amino acid residues 20 to 138, 139 to 182, 185 to 297, 299 to 364, and 365 to 434 of SEQ ID NO: 5, respectively. The amino acid sequence of the SP domain of an exemplary human MASP-3 is SEQ ID NO: 11, which corresponds to amino acid residues 450 to 728 of SEQ ID NO: 5.

The term "MASP-2," as used herein, refers to any native MASP-2 from any vertebrate source, including mammals such as primates (e.g. humans) and rodents (e.g., mice and rats), unless otherwise indicated. The term encompasses "full-length" unprocessed MASP-2 as well as any form of MASP-2 that results from processing in the cell. The term also encompasses naturally occurring variants of MASP-2, e.g., splice variants or allelic variants. The amino acid sequence of an exemplary human MASP-2 is shown in SEQ ID NO: 12.

Accession numbers for exemplary MASP-2 are as follows:
Human MASP-2 protein: NCBI RefSeq NP_006601
Human MASP-2 nucleotide: NCBI RefSeq NM_006610
Mouse MASP-2 protein: NCBI RefSeq NP_001003893, XP 358353
Mouse MASP-2 nucleotide: NCBI RefSeq NM_001003893 XM 358353

The amino acid sequence of the heavy/alpha chain of an exemplary human MASP-2 is SEQ ID NO: 13, which corresponds to amino acid residues 16 to 444 of SEQ ID NO: 12. The amino acid sequence of the SP domain of an exemplary human MASP-2 is SEQ ID NO: 14, which corresponds to amino acid residues 445 to 686 of SEQ ID NO: 12.

FIG. 1 shows comparison of the amino acid sequences of the SP domain of human MASP-1 (SEQ ID NO: 7) and the SP domain of human MASP-3 (SEQ ID NO: 11). FIG. 2 shows comparison of the amino acid sequences of the SP domains of human MASP-1 (SEQ ID NO: 7), monkey MASP-1 (SEQ ID NO: 8) and mouse MASP-1 (SEQ ID NO: 9). Identical amino acids are boxed.

The percent identities between the heavy/alpha and light/beta chains of the human MASP-1, MASP-2 and MASP-3 proteins are provided in Table 1 below. The percent amino acid sequence identities were determined by using ALIGN.

TABLE 1

|  | % identity between heavy/alpha chains | | | % identity between Light/beta chains | | |
| --- | --- | --- | --- | --- | --- | --- |
|  | hMASP-1 | hMASP-2 | hMASP-3 | hMASP-1 | hMASP-2 | hMASP-3 |
| hMASP-1 | 100% | 47.0% | 97.9% | 100% | 35.5% | 32.3% |
| hMASP-2 | 47.0% | 100% | 46.4% | 35.5% | 100% | 35.1% |
| hMASP-3 | 97.9% | 46.4% | 100% | 32.3% | 35.1% | 100% |

The percent identities between the SP domains of the human MASP-1, monkey MASP-1, mouse MASP-1 proteins are provided in Table 2 below. The percent amino acid sequence identities were determined by using ALIGN.

TABLE 2

|  | % identity between SP domains | | |
| --- | --- | --- | --- |
|  | Human MASP-1 | Monkey MASP-2 | Mouse MASP-3 |
| Human MASP-1 | 100% | 96.8% | 83.3% |
| Monkey MASP-2 | 96.8% | 100% | 82.1% |
| Mouse MASP-3 | 83.3% | 82.1% | 100% |

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-MASP-1 antibodies and uses thereof. In certain embodiments, antibodies that bind to MASP-1 are provided. Antibodies of the invention are useful, e.g., for the diagnosis or treatment of a disease caused by the complement lectin-pathway activation, preferably thrombotic microangiopathy (TMA), membranous nephropathy, age-related macular degeneration (AMD), myocardial infarctions, and/or stroke.

A. Exemplary Anti-MASP-1 Antibodies

In one aspect, the invention provides isolated antibodies that bind to MASP-1. In certain embodiments, an anti-MASP-1 antibody:
specifically binds to MASP-1
binds to an activated or inactivated form of MASP-1
binds to MASP-1 but does not or does not substantially bind to MASP-3
binds to the serine protease domain of MASP-1
inhibits activity of MASP-1 but does not inhibit activity of MASP-3
binds to the same etope as any anti-MASP-1 antibody described herein which is capable of binding to, and inhibiting activity of, human MASP-1, cynomolgus monkey MASP-1, and/or mouse MASP-1 inhibits C3 and/or C4 activation with an IC 50 of less than 0.35 micro g/mL.

In one aspect, the invention provides an anti-MASP-1 antibody comprising at least one, two, three, four, five, or six HVRs selected from (a) HVR-H1 comprising the amino acid sequence of SEQ ID NO: 32; (b) HVR-H2 comprising the amino acid sequence of SEQ ID NO: 33; (c) HVR-H3 comprising the amino acid sequence of SEQ ID NO: 34; (d) HVR-L1 comprising the amino acid sequence of SEQ ID NO: 35; (e) HVR-L2 comprising the amino acid sequence of SEQ ID NO: 36; and (f) HVR-L3 comprising the amino acid sequence of SEQ ID NO: 37.

In one aspect, the invention provides an anti-MASP-1 antibody comprising at least one, two, three, four, five, or six HVRs selected from (a) HVR-H1 comprising the amino acid sequence of SEQ ID NO: 38; (b) HVR-H2 comprising the amino acid sequence of SEQ ID NO: 39; (c) HVR-H3 comprising the amino acid sequence of SEQ ID NO: 40; (d) HVR-L1 comprising the amino acid sequence of SEQ ID NO: 41; (e) HVR-L2 comprising the amino acid sequence of SEQ ID NO: 42; and (f) HVR-L3 comprising the amino acid sequence of SEQ ID NO: 43.

In one aspect, the invention provides an anti-MASP-1 antibody comprising at least one, two, three, four, five, or six HVRs selected from (a) HVR-H1 comprising the amino acid sequence of SEQ ID NO: 44; (b) HVR-H2 comprising the amino acid sequence of SEQ ID NO: 45; (c) HVR-H3 comprising the amino acid sequence of SEQ ID NO: 46; (d) HVR-L1 comprising the amino acid sequence of SEQ ID NO: 47; (e) HVR-L2 comprising the amino acid sequence of SEQ ID NO: 48; and (f) HVR-L3 comprising the amino acid sequence of SEQ ID NO: 49.

In one aspect, the invention provides an anti-MASP-1 antibody comprising at least one, two, three, four, five, or six HVRs selected from (a) HVR-H1 comprising the amino acid sequence of SEQ ID NO: 50; (b) HVR-H2 comprising the amino acid sequence of SEQ ID NO: 51; (c) HVR-H3 comprising the amino acid sequence of SEQ ID NO: 52; (d) HVR-L1 comprising the amino acid sequence of SEQ ID NO: 53; (e) HVR-L2 comprising the amino acid sequence of SEQ ID NO: 54; and (f) HVR-L3 comprising the amino acid sequence of SEQ ID NO: 55.

In one aspect, the invention provides an anti-MASP-1 antibody comprising at least one, two, three, four, five, or six HVRs selected from (a) HVR-H1 comprising the amino acid sequence of SEQ ID NO: 56; (b) HVR-H2 comprising the amino acid sequence of SEQ ID NO: 57; (c) HVR-H3 comprising the amino acid sequence of SEQ ID NO: 58; (d) HVR-L1 comprising the amino acid sequence of SEQ ID NO: 59; (e) HVR-L2 comprising the amino acid sequence of SEQ ID NO: 60; and (f) HVR-L3 comprising the amino acid sequence of SEQ ID NO: 61.

In one aspect, the invention provides an anti-MASP-1 antibody comprising at least one, two, three, four, five, or six HVRs selected from (a) HVR-H1 comprising the amino acid sequence of SEQ ID NO: 62; (b) HVR-H2 comprising the amino acid sequence of SEQ ID NO: 63; (c) HVR-H3 comprising the amino acid sequence of SEQ ID NO: 64; (d) HVR-L1 comprising the amino acid sequence of SEQ ID NO: 65; (e) HVR-L2 comprising the amino acid sequence of SEQ ID NO: 66; and (f) HVR-L3 comprising the amino acid sequence of SEQ ID NO: 67.

In another aspect, an antibody of the invention comprises (a) a VH domain comprising at least one, at least two, or all three VH HVR sequences selected from (i) HVR-H1 comprising the amino acid sequence of SEQ ID NO: 32, (ii) HVR-H2 comprising the amino acid sequence of SEQ ID NO: 33, and (iii) HVR-H3 comprising an amino acid sequence of SEQ ID NO: 34; and (b) a VL domain comprising at least one, at least two, or all three VL HVR sequences selected from (i) HVR-L1 comprising the amino acid sequence of SEQ ID NO: 35, (ii) HVR-L2 comprising the amino acid sequence of SEQ ID NO: 36, and (c) HVR-L3 comprising the amino acid sequence of SEQ ID NO: 37.

In another aspect, an antibody of the invention comprises (a) a VH domain comprising at least one, at least two, or all three VH HVR sequences selected from (i) HVR-H1 comprising the amino acid sequence of SEQ ID NO: 38, (ii) HVR-H2 comprising the amino acid sequence of SEQ ID NO: 39, and (iii) HVR-H3 comprising an amino acid sequence of SEQ ID NO: 40; and (b) a VL domain comprising at least one, at least two, or all three VL HVR sequences selected from (i) HVR-L1 comprising the amino acid sequence of SEQ ID NO: 41, (ii) HVR-L2 comprising the amino acid sequence of SEQ ID NO: 42, and (c) HVR-L3 comprising the amino acid sequence of SEQ ID NO: 43.

In another aspect, an antibody of the invention comprises (a) a VH domain comprising at least one, at least two, or all three VH HVR sequences selected from (i) HVR-H1 comprising the amino acid sequence of SEQ ID NO: 44, (ii) HVR-H2 comprising the amino acid sequence of SEQ ID NO: 45, and (iii) HVR-H3 comprising an amino acid sequence of SEQ ID NO: 46; and (b) a VL domain comprising at least one, at least two, or all three VL HVR sequences selected from (i) HVR-L1 comprising the amino acid sequence of SEQ ID NO: 47, (ii) HVR-L2 comprising the amino acid sequence of SEQ ID NO: 48, and (c) HVR-L3 comprising the amino acid sequence of SEQ ID NO: 49.

In another aspect, an antibody of the invention comprises (a) a VH domain comprising at least one, at least two, or all three VH HVR sequences selected from (i) HVR-H1 comprising the amino acid sequence of SEQ ID NO: 50, (ii) HVR-H2 comprising the amino acid sequence of SEQ ID NO: 51, and (iii) HVR-H3 comprising an amino acid sequence of SEQ ID NO: 52; and (b) a VL domain comprising at least one, at least two, or all three VL HVR sequences selected from (i) HVR-L1 comprising the amino acid sequence of SEQ ID NO: 53, (ii) HVR-L2 comprising the amino acid sequence of SEQ ID NO: 54, and (c) HVR-L3 comprising the amino acid sequence of SEQ ID NO: 55.

In another aspect, an antibody of the invention comprises (a) a VH domain comprising at least one, at least two, or all three VH HVR sequences selected from (i) HVR-H1 comprising the amino acid sequence of SEQ ID NO: 56, (ii) HVR-H2 comprising the amino acid sequence of SEQ ID NO: 57, and (iii) HVR-H3 comprising an amino acid sequence of SEQ ID NO: 58; and (b) a VL domain comprising at least one, at least two, or all three VL HVR sequences selected from (i) HVR-L1 comprising the amino acid sequence of SEQ ID NO: 59, (ii) HVR-L2 comprising the amino acid sequence of SEQ ID NO: 60, and (c) HVR-L3 comprising the amino acid sequence of SEQ ID NO: 61.

In another aspect, an antibody of the invention comprises (a) a VH domain comprising at least one, at least two, or all three VH HVR sequences selected from (i) HVR-H1 comprising the amino acid sequence of SEQ ID NO: 62, (ii)

HVR-H2 comprising the amino acid sequence of SEQ ID NO: 63, and (iii) HVR-H3 comprising an amino acid sequence of SEQ ID NO: 64; and (b) a VL domain comprising at least one, at least two, or all three VL HVR sequences selected from (i) HVR-L1 comprising the amino acid sequence of SEQ ID NO: 65, (ii) HVR-L2 comprising the amino acid sequence of SEQ ID NO: 66, and (c) HVR-L3 comprising the amino acid sequence of SEQ ID NO: 67.

In another aspect, the invention provides an antibody comprising (a) HVR-H1 comprising the amino acid sequence of SEQ ID NO: 32; (b) HVR-H2 comprising the amino acid sequence of SEQ ID NO: 33; (c) HVR-H3 comprising the amino acid sequence of SEQ ID NO: 34; (d) HVR-L1 comprising the amino acid sequence of SEQ ID NO: 35; (e) HVR-L2 comprising the amino acid sequence of SEQ ID NO: 36; and (f) HVR-L3 comprising an amino acid sequence selected from SEQ ID NO: 37.

In another aspect, the invention provides an antibody comprising (a) HVR-H1 comprising the amino acid sequence of SEQ ID NO: 38; (b) HVR-H2 comprising the amino acid sequence of SEQ ID NO: 39; (c) HVR-H3 comprising the amino acid sequence of SEQ ID NO: 40; (d) HVR-L1 comprising the amino acid sequence of SEQ ID NO: 41; (e) HVR-L2 comprising the amino acid sequence of SEQ ID NO: 42; and (f) HVR-L3 comprising an amino acid sequence selected from SEQ ID NO: 43.

In another aspect, the invention provides an antibody comprising (a) HVR-H1 comprising the amino acid sequence of SEQ ID NO: 44; (b) HVR-H2 comprising the amino acid sequence of SEQ ID NO: 45; (c) HVR-H3 comprising the amino acid sequence of SEQ ID NO: 46; (d) HVR-L1 comprising the amino acid sequence of SEQ ID NO: 47; (e) HVR-L2 comprising the amino acid sequence of SEQ ID NO: 48; and (f) HVR-L3 comprising an amino acid sequence selected from SEQ ID NO: 49.

In another aspect, the invention provides an antibody comprising (a) HVR-H1 comprising the amino acid sequence of SEQ ID NO: 50; (b) HVR-H2 comprising the amino acid sequence of SEQ ID NO: 51; (c) HVR-H3 comprising the amino acid sequence of SEQ ID NO: 52; (d) HVR-L1 comprising the amino acid sequence of SEQ ID NO: 53; (e) HVR-L2 comprising the amino acid sequence of SEQ ID NO: 54; and (f) HVR-L3 comprising an amino acid sequence selected from SEQ ID NO: 55.

In another aspect, the invention provides an antibody comprising (a) HVR-H1 comprising the amino acid sequence of SEQ ID NO: 56; (b) HVR-H2 comprising the amino acid sequence of SEQ ID NO: 57; (c) HVR-H3 comprising the amino acid sequence of SEQ ID NO: 58; (d) HVR-L1 comprising the amino acid sequence of SEQ ID NO: 59; (e) HVR-L2 comprising the amino acid sequence of SEQ ID NO: 60; and (f) HVR-L3 comprising an amino acid sequence selected from SEQ ID NO: 61.

In another aspect, the invention provides an antibody comprising (a) HVR-H1 comprising the amino acid sequence of SEQ ID NO: 62; (b) HVR-H2 comprising the amino acid sequence of SEQ ID NO: 63; (c) HVR-H3 comprising the amino acid sequence of SEQ ID NO: 64; (d) HVR-L1 comprising the amino acid sequence of SEQ ID NO: 65; (e) HVR-L2 comprising the amino acid sequence of SEQ ID NO: 66; and (f) HVR-L3 comprising an amino acid sequence selected from SEQ ID NO: 67.

In any of the above embodiments, an anti-MASP-1 antibody is humanized. In one embodiment, an anti-MASP-1 antibody comprises HVRs as in any of the above embodiments, and further comprises an acceptor human framework, e.g. a human immunoglobulin framework or a human consensus framework.

In another aspect, an anti-MASP-1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20, 22, 24, 26, 28, or 30. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MASP-1 antibody comprising that sequence retains the ability to bind to MASP-1. In certain embodiments, a total of 1 to 10 amino acids have been substituted, inserted and/or deleted in SEQ ID NO: 20, 22, 24, 26, 28, or 30. In certain embodiments, substitutions, insertions, or deletions occur in regions outside the HVRs (i.e., in the FRs). Optionally, the anti-MASP-1 antibody comprises the VH sequence in SEQ ID NO: 20, 22, 24, 26, 28, or 30, including post-translational modifications of that sequence. Post-translational modifications include but are not limited to a modification of glutamine or glutamate in N-terminal of heavy chain or light chain to pyroglutamic acid by pyroglutamylation.

In another aspect, an anti-MASP-1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 21, 23, 25, 27, 29, or 31. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-PRO antibody comprising that sequence retains the ability to bind to PRO. In certain embodiments, a total of 1 to 10 amino acids have been substituted, inserted and/or deleted in SEQ ID NO: 21, 23, 25, 27, 29, or 31. In certain embodiments, the substitutions, insertions, or deletions occur in regions outside the HVRs (i.e., in the FRs). Optionally, the anti-MASP-1 antibody comprises the VL sequence in SEQ ID NO: 21, 23, 25, 27, 29, or 31, including post-translational modifications of that sequence. Post-translational modifications include but are not limited to a modification of glutamine or glutamate in N-terminal of heavy chain or light chain to pyroglutamic acid by pyroglutamylation.

In another aspect, an anti-MASP-1 antibody is provided, wherein the antibody comprises a VH as in any of the embodiments provided above, and a VL as in any of the embodiments provided above.

In a further aspect, the invention provides an antibody that binds to the same epitope as an anti-MASP-1 antibody provided herein. For example, in certain embodiments, an antibody is provided that binds to the same epitope as:

an anti-MASP-1 antibody comprising (a) HVR-H1 comprising the amino acid sequence of SEQ ID NO: 32; (b) HVR-H2 comprising the amino acid sequence of SEQ ID NO: 33; (c) HVR-H3 comprising the amino acid sequence of SEQ ID NO: 34; (d) HVR-L1 comprising the amino acid sequence of SEQ ID NO: 35; (e) HVR-L2 comprising the amino acid sequence of SEQ ID NO: 36; and (f) HVR-L3 comprising an amino acid sequence selected from SEQ ID NO: 37, an anti-MASP-1 antibody comprising (a) HVR-H1 comprising the amino acid sequence of SEQ ID NO: 38; (b) HVR-H2 comprising the amino acid sequence of SEQ ID NO: 39; (c) HVR-H3 comprising the amino acid sequence of SEQ ID NO: 40; (d) HVR-L1 comprising the amino acid sequence of SEQ ID NO: 41; (e) HVR-L2 comprising the amino acid sequence of SEQ ID NO: 42; and (f) HVR-L3 comprising an amino acid sequence selected from SEQ ID NO: 43, an anti-MASP-1 antibody comprising (a) HVR-H1 comprising the amino acid sequence of SEQ ID NO: 44; (b) HVR-H2 comprising the amino acid sequence of SEQ ID NO: 45; (c) HVR-H3 comprising the amino acid sequence of SEQ ID NO: 46; (d) HVR-L1 comprising the amino acid sequence of SEQ ID NO: 47; (e) HVR-L2 comprising the amino acid sequence of SEQ ID NO: 48; and (f) HVR-L3 comprising an amino acid sequence selected from SEQ ID NO: 49, an anti-MASP-1 antibody comprising (a) HVR-H1 comprising the amino acid sequence of SEQ ID NO: 50; (b) HVR-H2 comprising the amino acid sequence of SEQ ID NO: 51; (c) HVR-H3 comprising the amino acid sequence of SEQ ID NO: 52; (d) HVR-L1 comprising the amino acid sequence of SEQ ID NO: 53; (e) HVR-L2 comprising the amino acid sequence of SEQ ID NO: 54; and (f) HVR-L3 comprising an amino acid sequence selected from SEQ ID NO: 55, an anti-MASP-1 antibody comprising (a) HVR-H1 comprising the amino acid sequence of SEQ ID NO: 56; (b) HVR-H2 comprising the amino acid sequence of SEQ ID NO: 57; (c) HVR-H3 comprising the amino acid sequence of SEQ ID NO: 58; (d) HVR-L1 comprising the amino acid sequence of SEQ ID NO: 59; (e) HVR-L2 comprising the amino acid sequence of SEQ ID NO: 60; and (f) HVR-L3 comprising an amino acid sequence selected from SEQ ID NO: 61, or an anti-MASP-1 antibody comprising (a) HVR-H1 comprising the amino acid sequence of SEQ ID NO: 62; (b) HVR-H2 comprising the amino acid sequence of SEQ ID NO: 63; (c) HVR-H3 comprising the amino acid sequence of SEQ ID NO: 64; (d) HVR-L1 comprising the amino acid sequence of SEQ ID NO: 65; (e) HVR-L2 comprising the amino acid sequence of SEQ ID NO: 66; and (f) HVR-L3 comprising an amino acid sequence selected from SEQ ID NO: 67.

In a further aspect, the invention provides an antibody that binds to the same epitope as an anti-MASP-1 antibody provided herein. For example, in certain embodiments, an antibody is provided that binds to the same epitope as:
  an anti-MASP-1 antibody comprising a VH sequence of SEQ ID NO: 20 and a VL sequence of SEQ ID NO: 21,
  an anti-MASP-1 antibody comprising a VH sequence of SEQ ID NO: 22 and a VL sequence of SEQ ID NO: 23,
  an anti-MASP-1 antibody comprising a VH sequence of SEQ ID NO: 24 and a VL sequence of SEQ ID NO: 25,
  an anti-MASP-1 antibody comprising a VH sequence of SEQ ID NO: 26 and a VL sequence of SEQ ID NO: 27,
  an anti-MASP-1 antibody comprising a VH sequence of SEQ ID NO: 28 and a VL sequence of SEQ ID NO: 29, or
  an anti-MASP-1 antibody comprising a VH sequence of SEQ ID NO: 30 and a VL sequence of SEQ ID NO: 31.

In certain embodiments, an antibody that binds to an epitope within the serine protease (SP) domain of human MASP-1 (SEQ ID NO: 7) is provided.

In a further aspect of the invention, an anti-MASP-1 antibody according to any of the above embodiments is a monoclonal antibody, including a chimeric, humanized or human antibody. In one embodiment, an anti-MASP-1 antibody is an antibody fragment, e.g., a Fv, Fab, Fab', scFv, diabody, or F(ab')$_2$ fragment. In another embodiment, the antibody is a full length antibody, e.g., an intact IgG1, IgG2 or IgG4 antibody or other antibody class or isotype as defined herein.

In a further aspect, an anti-MASP-1 antibody according to any of the above embodiments may incorporate any of the features, singly or in combination, as described in Sections 1-13 below:

1. Antibody which Binds to MASP-1 but does not Bind to MASP-3

In certain embodiments, an antibody that specifically binds to MASP-1 is provided. In another embodiments, an anti-MASP-1 antibody binds to MASP-1 but does not bind to MASP-3. In another embodiments, an anti-MASP-1 antibody binds to MASP-1 but does not substantially bind to MASP-3.

Examples of monoclonal antibodies which bind to MASP-1 are described below in Table 3. All monoclonal antibodies which bind to MASP-1 in Table 3 also bind to MASP-3.

TABLE 3

| Antigen | Antibody Type | Reference |
|---|---|---|
| hMASP-1 (full-length) | Mouse mAbs; mAb 1E2 and 2B11 (both Abs recognize the heavy chain common to both MASP-1 and MASP-3) | Terai I. et al., *Clin Exp Immunol* 110: 317-323 (1997); mAb 1E2: Commercially available from Hycult Biotech Cat#HM2092 mAb 2B11: Commercially available from Hycult Biotech: Cat#HM2093 |
| hMASP-1 (full-length) | Mouse mAb 4C2 | Endo M. et al., *Nephrol Dial Transplant* 13: 1984-1990 (1998); mAb 4C2 is reported as mouse mAb directed against MASP-1/3 heavy chain in Roos A., et al., J Am Soc Nephrol. 2006 June; 17(6): 1724-34. |
| hMASP-1 (full-length) | MASP-1 chicken Abs; mAb D14 and 1E10 (both Abs recognize the heavy chain common to both MASP-1 and MASP-3) | WO2013/180834 (Example 15), and WO2013/192240 (Example 15); MASP-1 specific antibody is not actually obtained. |

In certain aspects, an anti-MASP-1 antibody does not bind, or does not substantially bind to MASP-3. In certain embodiments, an anti-MASP-1 antibody binds to MASP-1 with higher affinity than to MASP-3. In certain embodiments, the antibodies of the present invention bind to MASP-1 with at least 2, 3, 5, 10, 15, 20, 25, 30, 35, 40, 45, 50, 55, 60, 65, 70, 75, 80, 85, 90, 95, 100, 200, 400, 1000, 10000, 100000 or more times higher affinity than to MASP-3 when compared, e.g., on the basis of dissociation constant (Kd). In certain embodiments, the binding of the antibody to the MASP-3 protein is less than about 50%, 40%, 30%, 20% or 10% of the binding of the antibody to MASP-1 as measured, e.g., by a radioimmunoassay (RIA) or Enzyme-Linked ImmunoSorbent Assay (ELISA).

As described herein, the inventors have unexpectedly discovered monoclonal antibodies which bind to MASP-1 but do not bind to MASP-3. The inventors have also confirmed that the monoclonal antibodies which bind to MASP-1 but do not bind to MASP-3 have inhibition activity against MASP-1. WO2013/180834 discloses selection methods for MASP-1 antigen binding (Example 15 of WO2013/180834), the methods comprising parallel screens for binders to MASP-1 and MASP-3 using (i) the heavy/alpha chain which is shared between MASP-1 and MASP-3 and (ii) the distinct light/beta chains comprising a serine protease domain. However, no monoclonal antibodies which specifically bind to MASP-1 have been actually obtained. It has been reported that the catalytic activity of MASP-1 suppresses its expression through rapid auto-activation and auto-degradation (Protein Expr Purif Vol 88, Issue 2, April 2013, pp 173-182). Also, MASP-1 is known to be able to auto-activate and, owing to its high activity, MASP-1 furthermore seems prone to auto-degradation. Because the light/beta-chain (the serine protease domain) of MASP-1 is a part of the MASP-1 catalytic region (CCP1-CCP2-SP domains), it has been difficult to purify or produce a stable MASP-1 SP domain and to screen antibodies for binding to the SP domain of MASP-1.

2. Antibody which Binds to the SP (Serine Protease) Domain of MASP-1

In certain embodiments, an antibody that binds to an epitope within the serine protease (SP) domain of human MASP-1 (SEQ ID NO: 7) is provided.

MASP-1 and MASP-3 are alternative splicing variants of the MASP-1 gene. They contain an identical heavy/alpha chain (CUB1-EGF-CUB2-CCP1-CCP2 domains) prolonged by a different light/beta chain (SP domain) at the C-terminal end. Therefore, in certain embodiments, it is expected that an antibody which binds to MASP-1 but does not bind to MASP-3 binds or specifically binds to the SP domain of MASP-1.

In certain embodiments, an anti-MASP-1 antibody is an antibody which cross-reacts with human MASP-1, monkey MASP-1 and mouse MASP-1. In certain embodiments, an anti-MASP-1 antibody binds to an epitope of MASP-1 that is conserved among MASP-1 SP domains from human, monkey and mouse. In further embodiments, it is expected that an antibody which cross-reacts with human MASP-1, monkey MASP-1 and mouse MASP-1 binds to an epitope of MASP-1 that is conserved among MASP-1 SP domains from human, monkey and mouse. An exemplary amino acid sequence that is conserved among MASP-1 SP domains from human, monkey and mouse is amino acid residues 1 to 8, 13 to 34, 39 to 51, 60 to 69, 71 to 75, 100 to 104, 135 to 151, 153 to 161, 172 to 178, 180 to 204, 211 to 216, 223 to 236, or 239 to 245 of SEQ ID NO: 7. (FIG. 2)

3. Antibody which Binds to an Activated or Inactivated Form of MASP-1

In certain embodiments, an anti-MASP-1 antibody is an antibody that binds to the activated form of MASP-1. MASP-1 contains a heavy/alpha chain (CUB1-EGF-CUB2-CCP1-CCP2 domains) prolonged by a light/beta chain (SP domain) at the C-terminal end. MASP-1 is activated by cleavage in the activation peptide, separating the heavy/alpha chain and light/beta chain. The two chains are then held together by an interchain cysteine bridge (disulphide bridge). In certain embodiments, an anti-MASP-1 antibody inhibits more than 10%, 20%, 30%, 40%, 50%, 60%, 70%, 80% or 90% of MASP-1 enzymatic activity.

In certain embodiments, an anti-MASP-1 antibody is an antibody that binds to the activated form of MASP-1 but does not bind to the inactivated form of MASP-1. In certain embodiments, an anti-MASP-1 antibody is an antibody that binds to the inactivated form of MASP-1 but does not bind to the activated form of MASP-1. In certain embodiments, an anti-MASP-1 antibody is an antibody that binds to both the activated and inactivated forms of MASP-1.

4. Antibody which Inhibits LP (Lectin Pathway) of Complement Activation

In certain embodiments, an anti-MASP-1 antibody is an antibody that inhibits MASP-1 activity. In further embodiments, the MASP-1 activity is MASP-1-mediated complement lectin-pathway activation. Without intending to be bound by any theory, MASP-1 functions as a component of the lectin pathway of complement activation. Upon binding, MASP-1 will first autoactivate, then it activates MASP-2 and MASP-3. The activated MASP-2 cleaves C4 into C4a, C4b, and C4c, while activated MASP-1 and MASP-2 cleave C2 into C2a, and C2b. The assembly of the C4a and C2b fragments results in the formation of the C3 convertase C4bC2a. The C4bC2a cleaves C3 into C3a and C3b, followed by cleavage of C3b into C3c and C3d by Factor I. In certain embodiments, an anti-MASP-1 antibody binds to MASP-1 and inhibits MASP-1 activity to activate MASP-2 and MASP-3. In further embodiments, an anti-MASP-1 antibody binds to MASP-1 and inhibits activation of the lectin pathway.

In certain embodiments, an anti-MASP-1 antibody inhibits activation of the lectin pathway with an IC 50 of less than 0.5 micro g/mL, 0.45 micro g/mL, 0.40 micro g/mL, 0.35 micro g/mL, 0.34 micro g/mL, 0.33 micro g/mL, 0.32 micro g/mL, 0.31 micro g/mL, 0.3 micro g/mL, 0.29 micro g/mL, 0.28 micro g/mL, 0.27 micro g/mL, 0.26 micro g/mL, 0.25 micro g/mL, 0.24 micro g/mL, 0.23 micro g/mL, 0.22 micro g/mL, 0.21 micro g/mL, 0.2 micro g/mL, 0.19 micro g/mL, 0.18 micro g/mL, 0.17 micro g/mL, 0.16 micro g/mL, 0.15 micro g/mL, 0.14 micro g/mL, 0.13 micro g/mL or 0.12 micro g/mL, preferably less than 0.35 micro g/mL, 0.34 micro g/mL, 0.33 micro g/mL, 0.32 micro g/mL, 0.31 micro g/mL or 0.3 micro g/mL, more preferably less than 0.35 micro g/mL.

5. Antibody which Inhibits MASP-1 Activity but does not Inhibit MASP-3 Activity

In certain embodiments, an anti-MASP-1 antibody is an antibody that inhibits MASP-1 activity but does not directly inhibit MASP-3 activity. An antibody that directly inhibits MASP-3 is an antibody which binds to MASP-3 and inhibits its activity, while an antibody that indirectly inhibits MASP-3 is an antibody which binds to a molecule other than MASP3 and inhibits MASP-3 activity (e.g., an anti-MASP-1 antibody that inhibits MASP-3 activation). It has been reported that MASP-1 activates MASP-3, which converts the alternative pathway activation enzyme factor D from its zymogen form into its enzymatically active form (J. Immunol. 187:3751-58 (2011)). Methods to assess the activation of factor D are already known in the art (e.g., J Immunol Jan. 15, 2016, 196 (2) 857-865)

6. Stable Anti-MASP-1 Antibody

In certain embodiments, an anti-MASP-1 antibody is stable after being incubated in PBS at 40 degrees C. for 1 week, 2 weeks or more. The term "stable" as used herein means that the anti-MASP-1 antibody after incubation has MASP-1 inhibition activity which is substantially similar to the anti-MASP-1 antibody before incubation. The term "stable" as used herein means that the anti-MASP-1 antibody after incubation has more than 50%, 60%, 70%, 80% or 90% of MASP-1 inhibition activity of the anti-MASP-1 antibody before incubation.

7. Antibody Affinity

In certain embodiments, an antibody provided herein has a dissociation constant (Kd) of 1 micro M or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$M, e.g., from $10^{-9}$M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER (registered trademark) multi-well plates (Thermo Scientific) are coated overnight with 5 micro g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 micro 1/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE (registered trademark)-3000 (BIAcore, Inc., Piscataway, NJ) is performed at 25 degrees C. with immobilized antigen CMS chips at ~10 response units (RU). In one embodiment, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (~0.2 micro M) before injection at a flow rate of 5 micro 1/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro 1/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

8. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

9. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing");

Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

10. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB (registered trademark) technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

11. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

12. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for MASP-1 and the other is for any other antigen. In certain embodiments, bispecific antibodies may bind to two different epitopes of MASP-1. Bispecific antibodies may also be used to localize cytotoxic agents to cells which express MASP-1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to MASP-1 as well as another, different antigen (see, US 2008/0069820, for example).

13. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 4 under the heading of "preferred substitutions." More substantial changes are provided in Table 4 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 4

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE 4-continued

| Original Residue | Exemplary Substitutions | Preferred Substitutions |
|---|---|---|
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding ability. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96 (registered trademark) non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with increased or decreased binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either increased or decreased) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and increased binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-MASP-1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-MASP-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-MASP-1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

C. Assays

Anti-MASP-1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding to MASP-1 with any anti-MASP-1 antibody described herein. In certain embodiments, such a competing antibody binds to the same epitope (e.g., a linear or a conformational epitope) that is bound by an anti-MASP-1 antibody described herein. Detailed exemplary methods for mapping an epitope to which an antibody binds are provided in Morris (1996) "Epitope Mapping Protocols," in Methods in Molecular Biology vol. 66 (Humana Press, Totowa, NJ).

In an exemplary competition assay, immobilized MASP-1 is incubated in a solution comprising a first labeled antibody that binds to MASP-1 and a second unlabeled antibody that is being tested for its ability to compete with the first antibody for binding to MASP-1. The second antibody may be present in a hybridoma supernatant. As a control, immobilized MASP-1 is incubated in a solution comprising the first labeled antibody but not the second unlabeled antibody. After incubation under conditions permissive for binding of the first antibody to MASP-1, excess unbound antibody is removed, and the amount of label associated with immobilized MASP-1 is measured. If the amount of label associated with immobilized MASP-1 is substantially reduced in the test sample relative to the control sample, then that indicates that the second antibody is competing with the first antibody for binding to MASP-1. See Harlow and Lane (1988) Antibodies: A Laboratory Manual ch. 14 (Cold Spring Harbor Laboratory, Cold Spring Harbor, NY).

2. Activity Assays

In one aspect, assays are provided for identifying anti-MASP-1 antibodies thereof having biological activity. Biological activity may include, e.g., an inhibitory activity against MASP-1. Antibodies having such biological activity in vivo and/or in vitro are also provided.

In certain embodiments, an antibody of the invention is tested for such biological activity.

In certain embodiments, an antibody of the invention is tested for its cross-reactivity against MASP-1 and MASP-3 by, for example, known binding assays such as ELISA, radioimmunoassay (RIA), Western blot, BIACORE (registered trademark), etc. In certain embodiments, an antibody that binds to MASP-1 with at least 2, 3, 5, 10, 15, 20, 25, 30, 35, 40, 45, 50, 55, 60, 65, 70, 75, 80, 85, 90, 95, 100, 200, 400, 1000, 10000, 100000 or more times higher affinity than to MASP-3 when compared, e.g., on the basis of dissociation constant (Kd), is selected. In certain embodiments, an antibody whose binding to MASP-3 is less than about 50%, 40%, 30%, 20% or 10% of the binding of the antibody to MASP-1 as measured, e.g., by a radioimmunoassay (RIA) or Enzyme-Linked ImmunoSorbent Assay (ELISA), is selected.

In certain embodiments, an antibody of the invention is tested for its inhibitory activity on the lectin pathway of the complement system. The inhibitory activity of a test antibody against the lectin pathway of complement activation can be determined by, for example, detecting and/or measuring deposition of a complement component (e.g., C4c, C3c, or such) generated through the lectin pathway. Such detection methods are known, for example, as described in Petersen et al., Journal of Immunological Methods 257: 107-116 (2001). In an exemplary detection method, a test antibody is contacted with normal serum in vitro and incubated in a mannan-coated plate, and the deposition of C4c or C3c is detected and/or measured by conventional methods such as ELISA. Alternatively, a test antibody is contacted with normal serum in vivo by administering it to an animal. Blood is collected from the animal and centrifuged to separate serum, and the separated serum is incubated in a mannan-coated plate to detect and/or measure C4c or C3c deposition as described above. If the C4c or C3c deposition is reduced by the test antibody as compared to a negative control, the test antibody is determined to have inhibitory activity on the lectin pathway of complement activation. In certain embodiments, an antibody of the invention may inhibit the lectin pathway of complement activation by at least 5%, 10%, 15%, 20%, 25%, 30%, 35%, 40%, 45%, 50%, 55%, 60%, 65%, 70%, 75%, 80%, 85%, 90%, or 95% or greater as compared to a negative control as measured in the assay. Based on results of the assay, IC50 values may be calculated using appropriate analysis software such as GraphPad Prism (registered trademark).

In certain embodiments, an antibody of the invention is tested for its inhibitory activity on the enzymatic activity of the active form of MASP-1. The enzymatic activity of the active form of MASP-1 includes, but is not limited to, endopeptidase activity. The inhibitory activity of a test antibody against the enzymatic activity of the active form of MASP-1 can be detected and/or measured by, for example, a peptide cleavage assay as described in, e.g., Degn et al., Protein Expression and Purification 88: 173-182 (2013). In an exemplary method, an artificial fluorogenic peptide substrate such as Boc-VPR-AMC is used as a substrate for MASP-1. The peptide substrate is allowed to react with MASP-1 in the presence of a test antibody, and cleavage of the peptide is measured as relative fluorescence intensity. If the fluorescence is reduced in the presence of the test antibody as compared to that in the absence of the test antibody, the test antibody is determined to have inhibitory activity on the enzymatic activity of MASP-1. In certain embodiments, an antibody of the invention may inhibit the enzymatic activity of the active form of MASP-1 by at least 5%, 10%, 15%, 20%, 25%, 30%, 35%, 40%, 45%, 50%, 55%, 60%, 65%, 70%, 75%, 80%, 85%, 90%, or 95% or greater as compared to a negative control as measured in the assay.

D. Immunoconjugates

The invention also provides immunoconjugates comprising an anti-MASP-1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

E. Methods and Compositions for Diagnostics and Detection

In certain embodiments, any of the anti-MASP-1 antibodies provided herein is useful for detecting the presence of MASP-1 in a biological sample. The term "detecting" as used herein encompasses quantitative or qualitative detection. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrum, mammary gland secretion, lymph, urine, sweat, lacrimal fluid, gastric fluid, synovial fluid, peritoneal fluid, ocular lens fluid or mucus.

In one embodiment, an anti-MASP-1 antibody for use in a method of diagnosis or detection is provided. In a further aspect, a method of detecting the presence of MASP-1 in a biological sample is provided. In certain embodiments, the method comprises contacting the biological sample with an anti-MASP-1 antibody as described herein under conditions permissive for binding of the anti-MASP-1 antibody to MASP-1, and detecting whether a complex is formed between the anti-MASP-1 antibody and MASP-1. Such method may be an in vitro or in vivo method. In one embodiment, an anti-MASP-1 antibody is used to select subjects eligible for therapy with an anti-MASP-1 antibody, e.g. where MASP-1 is a biomarker for selection of patients.

Exemplary disorders that may be diagnosed using an antibody of the invention include diseases caused by the complement lectin-pathway activation, such as thrombotic microangiopathy (TMA), membranous nephropathy, age-related macular degeneration (AMD), myocardial infarctions, and stroke.

In certain embodiments, labeled anti-MASP-1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, those coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-MASP-1 antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-MASP-1 antibodies provided herein may be used in therapeutic methods.

In one aspect, an anti-MASP-1 antibody for use as a medicament is provided. In further aspects, an anti-MASP-1 antibody for use in treating a disease caused by complement lectin-pathway activation is provided. In certain embodiments, an anti-MASP-1 antibody for use in a method of treatment is provided. In certain embodiments, the invention provides an anti-MASP-1 antibody for use in a method of treating an individual having a disease caused by complement lectin-pathway activation comprising administering to the individual an effective amount of the anti-MASP-1 antibody. In one such embodiment, the method further comprises administering to the individual an effective amount of at least one additional therapeutic agent, e.g., as described below. In further embodiments, the invention provides an anti-MASP-1 antibody for use in inhibiting complement lectin-pathway activation mediated by MASP-1. In certain embodiments, the invention provides an anti-MASP-1 antibody for use in a method of inhibiting complement lectin-pathway activation mediated by MASP-1 in an individual comprising administering to the individual an effective of the anti-MASP-1 antibody to inhibit complement lectin-pathway activation mediated by MASP-1. An "individual" according to any of the above embodiments is preferably a human. In further embodiments, the invention provides an anti-MASP-1 antibody for use in inhibiting C3 and/or C4 activation. In certain embodiments, the invention provides an anti-MASP-1 antibody for use in a method of inhibiting C3 and/or C4 activation in an individual comprising administering to the individual an effective of the anti-MASP-1 antibody to inhibit C3 and/or C4 activation. An "individual" according to any of the above embodiments is preferably a human.

In a further aspect, the invention provides for the use of an anti-MASP-1 antibody in the manufacture or preparation of a medicament. In one embodiment, the medicament is for treatment of a disease caused by complement lectin-pathway activation. In a further embodiment, the medicament is for use in a method of treating a disease caused by complement lectin-pathway activation comprising administering to an individual having a disease caused by complement lectin-pathway activation an effective amount of the medicament. In one such embodiment, the method further comprises administering to the individual an effective amount of at least one additional therapeutic agent, e.g., as described below. In a further embodiment, the medicament is for inhibiting complement lectin-pathway activation mediated by MASP-1. In a further embodiment, the medicament is for use in a method of inhibiting complement lectin-pathway activation mediated by MASP-1 in an individual comprising administering to the individual an amount effective of the medicament to inhibit complement lectin-pathway activation mediated by MASP-1. An "individual" according to any of the above embodiments may be a human. In a further embodiment, the medicament is for C3 and/or C4 activation. In a further embodiment, the medicament is for use in a method of C3 and/or C4 activation in an individual comprising administering to the individual an amount effective of the medicament to inhibit C3 and/or C4 activation. An "individual" according to any of the above embodiments may be a human.

In a further aspect, the invention provides a method for treating a disease caused by complement lectin-pathway activation. In one embodiment, the method comprises administering to an individual having such a disease caused by complement lectin-pathway activation an effective amount of an anti-MASP-1 antibody. In one such embodiment, the method further comprises administering to the individual an effective amount of at least one additional therapeutic agent, as described below. An "individual" according to any of the above embodiments may be a human.

In a further aspect, the invention provides a method for inhibiting complement lectin-pathway activation mediated by MASP-1 in an individual. In one embodiment, the method comprises administering to the individual an effective amount of an anti-MASP-1 antibody to inhibit complement lectin-pathway activation mediated by MASP-1. In one embodiment, an "individual" is a human.

In a further aspect, the invention provides a method for inhibiting C3 and/or C4 activation in an individual. In one embodiment, the method comprises administering to the individual an effective amount of an anti-MASP-1 antibody to inhibit C3 and/or C4 activation. In one embodiment, an "individual" is a human.

In a further aspect, the invention provides pharmaceutical formulations comprising any of the anti-MASP-1 antibodies provided herein, e.g., for use in any of the above therapeutic methods. In one embodiment, a pharmaceutical formulation comprises any of the anti-MASP-1 antibodies provided herein and a pharmaceutically acceptable carrier. In another embodiment, a pharmaceutical formulation comprises any of the anti-MASP-1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-MASP-1 antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 micro g/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-MASP-1 antibody.

H. Articles of Manufacture

In another aspect of the invention, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-MASP-1 antibody.

III. Examples

The following are examples of methods and compositions of the invention. It is understood that various other embodiments may be practiced, given the general description provided above.

Example 1

Expression and Purification of Recombinant Human MASP-1 (CCP1-CCP2-SP), Human MASP-1 (CCP1-CCP2-SP S646A), and Human MASP-3 (CCP1-CCP2-SP S664A)

Human MASP-1 (CCP1-CCP2-SP) (SEQ ID NO: 15) fused with a Flag-tag on its N-terminus was expressed transiently using FreeStyle293-F cell line (Thermo Fisher). Conditioned media expressing human MASP-1 (CCP1-CCP2-SP) was applied to a column packed with anti-Flag M2 affinity resin (Sigma) and eluted with Flag peptide (Sigma). Fractions containing human MASP-1 (CCP1-CCP2-SP) were collected and subsequently subjected to a Superdex 200 gel filtration column (GE healthcare) equilibrated with 1×PBS. Fractions containing human MASP-1 (CCP1-CCP2-SP) were then pooled and stored at −80 degrees C.

In order to prevent self-digestion, Ser at position 646 of human MASP-1 was substituted with Ala, and Ser at position 664 of MASP-3 was substituted with Ala. The human MASP-1 CCP1-CCP2-SP domain carrying the Ser646Ala mutation was designated as human MASP-1 (CCP1-CCP2-SP S646A) (SEQ ID NO: 16) and the human MASP-3 CCP1-CCP2-SP domain carrying the Ser664Ala mutation was designated as human MASP-3 (CCP1-CCP2-SP S664A) (SEQ ID NO: 17)). Position 646 of MASP-1 corresponds to the amino acid position 376 of SEQ ID NO: 15 and 16, and position 664 of human MASP-3 corresponds to the amino acid position 394 of SEQ ID NO: 17. Expression and purification of N-terminally Flag-tagged human MASP-1 (CCP1-CCP2-SP S646A) and N-terminally Flag-tagged human MASP-3 (CCP1-CCP2-SP S664A) were performed exactly the same way as N-terminally Flag-tagged human MASP-1 (CCP1-CCP2-SP).

Example 2

Expression and Purification of Recombinant Antibodies

Unless indicated otherwise, recombinant antibodies were expressed transiently using FreeStyle293-F cell line (Thermo Fisher). Purification from the conditioned media expressing the antibodies was done with a conventional method using protein A. Gel filtration was further conducted if necessary.

Example 3

Generation of Anti-MASP-1 Antibodies 3.1. Antibody Screening

Anti-MASP1 antibodies were prepared, selected and assayed as follows: Twelve to sixteen week old NZW rabbits were immunized intradermally with human MASP-1 (CCP1-CCP2-SP) or human MASP-1 (CCP1-CCP2-SP S646A) (50-100 micro g/dose/rabbit). This dose was repeated 3 times over 1 month. One week after the final immunization, the spleen and blood were collected from the immunized rabbits. Antigen-specific B-cells were stained with labelled antigen, sorted with FCM cell sorter (FACS aria III, BD), and plated in 96-well plates at a density of one cell/well together with 25,000 cells/well of EL4 cells (European Collection of Cell Cultures) and an activated rabbit T-cell conditioned medium diluted 20 times, and were cultured for 7-12 days. EL4 cells were treated with mitomycin C (Sigma, Cat No. M4287) for 2 hours and washed 3 times in advance. The activated rabbit T-cell conditioned medium was prepared by culturing rabbit thymocytes in RPMI-1640 containing Phytohemagglutinin-M (Roche, Cat No. 1 1082132-001), phorbol 12-myristate 13-acetate (Sigma, Cat No. P1585) and 2% FBS. After cultivation, B-cell culture supernatants were collected for further analysis and pellets were cryopreserved.

ELISA assay was used to test specificity of antibodies in B-cell culture supernatant. Streptavidin (GeneScript, Cat No. Z02043) was coated onto a 384-well MAXISorp (Nunc, Cat No. 164688) at 50 nM in PBS for 1 hour at room temperature. Plates were then blocked with Blocking One (Nacalai Tesque, Cat No. 03953-95) diluted 5 times. Human MASP-1 (CCP1-CCP2-SP S646A) was labelled with NHS-PEG4-Biotin (PIERCE, Cat No. 21329) and was added to the blocked ELISA plates, incubated for 1 hour and washed with PBS containing 0.05% Tween20. B-cell culture supernatants were added to the ELISA plates, incubated for 1 hour and washed. Binding was detected by goat anti-rabbit IgG-Horseradish peroxidase (BETHYL, Cat No. A120-111P) followed by the addition of ABTS (KPL, Cat No. 50-66-06).

A total of 15,524 B-cell lines were screened for binding to human MASP-1 (CCP1-CCP2-SP S646A) and 94 lines were selected and designated as MTA0095-0188. Their RNA was purified from cryopreserved cell pellets by using ZR-96 Quick-RNA kits (ZYMO RESEARCH, Cat No. R1053). The DNAs of their antibody heavy chain variable regions were amplified by reverse transcription PCR and recombined with the DNA encoding F760G4 (SEQ ID NO: 18), which is a modified human IgG4 heavy chain constant region with Fc gamma receptors (Fc gamma Rs) silent. The DNAs of their antibody light chain variable regions were amplified by reverse transcription PCR and recombined with the DNA encoding kOMTC (SEQ ID NO: 19), which is a modified human kappa light chain constant region. Cloned antibodies were expressed in FreeStyle™ 293-F Cells (Invitrogen) and purified from culture supernatant to evaluate functional activity. Inhibiting activities of the chimeric monoclonal antibodies against human MASP-1 were evaluated by testing inhibition of hC4c (human C4c) deposition assay as described later (Example 4).

3.2 Cross-Reactivity Against Human MASP-1 and Human MASP-3

ELISA assay was used to check the cross-reactivity of the chimeric monoclonal antibodies generated in 3.1 against human MASP-1 and human MASP-3. Goat anti-human IgG polyclonal antibody (Thermo Scientific, H10500) was diluted to 1 micro g/ml with PBS (−) and added to 384-well MAXISorp plates (Nunc, Cat No. 164688). The plates were incubated for 1 hour at room temperature, and blocked with Blocking One (Nacalai Tesque, Cat No. 03953-95) diluted 5 times. The plates were incubated for 1 hour, washed, and anti-MASP-1 antibody was added and incubated for 1 hour. Human MASP-1 (CCP1-CCP2-SP S646A) or human MASP-3 (CCP1-CCP2-SP S664A) was labelled with NHS-PEG4-Biotin (PIERCE, Cat No. 21329). After incubation, the plates were washed and 8 nM of labeled antigen was added and incubated for 1 hour. After incubation, the plates were washed and Streptavidin-HRP conjugate (Thermo Scientific 21130) were added. After 1 hour incubation, binding of biotinylated antigen was detected by the addition of ABTS (KPL, Cat No. 50-66-06). Anti-MASP-1 monoclonal antibodies listed in Table 5 were selected as MASP-1 specific antibodies and used for further analysis. The sequences of the variable regions and the HVRs of the selected antibodies are shown in Tables 6 and 7, respectively.

TABLE 5

Specific binding of selected monoclonal antibodies against human MASP-1 (CCP1-CCP2-SP S646A)

| Antibody | Human MASP-1 (CCP1-CCP2-SP S646A) | Human MASP-3 (CCP1-CCP2-SP S664A) |
|---|---|---|
| MAS0102dd | 1.9795 | −0.027 |
| MAS0114bb | 1.7905 | −0.068 |
| MAS0116aa | 1.7195 | 0.055 |
| MAS0141aa | 1.5095 | −0.147 |
| MAS0154dd | 1.9515 | 0.078 |
| MAS0177hh | 0.8985 | 0.388 |

The values show absorbance at 405 nm after background subtraction.

TABLE 6

Sequences of variable regions of selected monoclonal antibodies

| Antibody | Variable Region | SEQ ID NO |
|---|---|---|
| MAS0102dd | Heavy chain variable region | 20 |
| | Light chain variable region | 21 |
| MAS0114bb | Heavy chain variable region | 22 |
| | Light chain variable region | 23 |
| MAS0116aa | Heavy chain variable region | 24 |
| | Light chain variable region | 25 |
| MAS0141aa | Heavy chain variable region | 26 |
| | Light chain variable region | 27 |
| MAS0154dd | Heavy chain variable region | 28 |
| | Light chain variable region | 29 |
| MAS0177hh | Heavy chain variable region | 30 |
| | Light chain variable region | 31 |

TABLE 7

Sequences of HVRs of selected antibodies

| Antibody | HVR | Sequence | SEQ ID NO |
|---|---|---|---|
| MAS0102dd | HVR H1 | SYAMS | 32 |
| | HVR H2 | IITNLDNTYYANWAKG | 33 |
| | HVR H3 | ERIKRKYSYDDYGGWAFDP | 34 |
| | HVR L1 | QAIENIYRSLA | 35 |
| | HVR L2 | DTSDLAS | 36 |
| | HVR L3 | QSYYYSSVTYNA | 37 |
| MAS0114bb | HVR H1 | NYAIH | 38 |
| | HVR H2 | YIYARSGVTWYASWVKG | 39 |
| | HVR H3 | VLAGGGYANTGLSL | 40 |
| | HVR L1 | QASQNIGYSSA | 41 |
| | HVR L2 | GASTLAS | 42 |
| | HVR L3 | QSNYISSGSVDGT | 43 |
| MAS0116aa | HVR H1 | SCYMS | 44 |
| | HVR H2 | TIYTGSGATYYASWAKG | 45 |
| | HVR H3 | AIYPGSSSSNLCAFDL | 46 |
| | HVR L1 | QASQSVYDNNWLA | 47 |
| | HVR L2 | QASSLAS | 48 |
| | HVR L3 | QGYYAGVLYS | 49 |
| MAS0141aa | HVR H1 | NYYMT | 50 |
| | HVR H2 | IINTDGGTYYASWAKG | 51 |
| | HVR H3 | GVFTGGWTGMRTNL | 52 |

TABLE 7-continued

Sequences of HVRs of selected antibodies

| Antibody | HVR | Sequence | SEQ ID NO |
|---|---|---|---|
| | HVR L1 | QASEDIYILLA | 53 |
| | HVR L2 | AASNLES | 54 |
| | HVR L3 | QCTYGSSSSNA | 55 |
| MAS0154dd | HVR H1 | NYNMG | 56 |
| | HVR H2 | IISSQGDIYYATWAKG | 57 |
| | HVR H3 | ARHVGSAADSYFHL | 58 |
| | HVR L1 | QASEEIYRNLA | 59 |
| | HVR L2 | GASNLAS | 60 |
| | HVR L3 | QRYAWGKNSADGNT | 61 |
| MAS0177hh | HVR H1 | SAYMN | 62 |
| | HVR H2 | IIYASGSTWYASWAKG | 63 |
| | HVR H3 | DDYGTADL | 64 |
| | HVR L1 | QASQSIGSSLA | 65 |
| | HVR L2 | GASTLVS | 66 |
| | HVR L3 | QNYYLSSSSADRRT | 67 |

Example 4

4.1 Inhibition of Lectin Pathway by Anti-MASP-1 Monoclonal Antibodies

The lectin pathway (LP) is activated upon binding of mannan-binding lectin (MBL) to mannan. The MBL is subsequently associated with MASPs. Without intending to be bound by any theory, upon binding, MASP-1 will first autoactivate and then it activates MASP-2 and MASP-3. The activated MASP-2 cleaves C4 into C4a, C4b, and C4c, while activated MASP-1 and MASP-2 cleave C2 into C2a, and C2b. The assembly of the C4a and C2b fragments results in the formation of the C3 convertase C4bC2a. The C4bC2a cleaves C3 into C3a and C3b, followed by cleavage of C3b into C3c and C3d by Factor I. The anti-MASP-1 chimeric mAbs obtained in Example 3 were tested for inhibition of the lectin pathway of the complement system by C4c or C3c ELISA assay. Mannan (20 micro g/mL) was coated on 96-well plates at 4 degrees C. overnight. The plates were blocked with TBS blocking buffer (Block Ace Powder, DS Pharma Biomedical) containing 0.5% bovine serum albumin (Roche Diagnostics) for 2 hours at 37 degrees C. Fifty-five microliters of normal human serum (4%) (Biopredic, SER019) was mixed with 55 micro L of diluted anti-MASP-1 mAb in a 96-well plate and incubated on a shaker for 1 hour at 25 degrees C. Serum samples containing anti-MASP-1 mab were transferred into the mannan-coated plates and incubated for 1 hour at 37 degrees C. After washing the plates, 100 micro L of rabbit anti-human C4c (Dako) was added to each well and reacted for 1 hour at R/T. Then the plates were washed and C4c deposition was detected by goat anti-rabbit IgG-Horseradish peroxidase (BETHYL) followed by the addition of ABTS (KPL). FIGS. 3A-3C shows data indicating that anti-MASP-1 mAbs: MAS0102dd, MAS0114bb, MAS0116aa, MAS0154dd, and MAS0177hh, inhibited human C4c deposition. Similarly, these antibodies inhibited cynomolgus monkey C3c deposition (FIG. 3B). All of the antibodies except MAS0116aa inhibited mouse C4c deposition as well (FIG. 3C).

4.2 IC 50 Values of Anti-MASP-1 mAbs

From the result of C4c ELISA assay using human serum described in 4.1, the IC50 value of each chimeric monoclonal antibody was calculated with GraphPad Prism (registered trademark). The calculated IC50 values are shown in Table 8.

TABLE 8

| Antibody | IC50 (µg/mL) |
|---|---|
| MAS0102dd | 0.29 |
| MAS0114bb | 0.14 |
| MAS0116aa | 0.47 |
| MAS0141aa | 0.45 |
| MAS0154dd | 0.11 |
| MAS0177hh | 3.29 |

4.3 Stability of Anti-MASP-1 mAb

The anti-MASP-1 chimeric mAb: MAS0141aa, was incubated in PBS at 40 degrees C. for 2 weeks to evaluate the stability of the antibody. After the 2-week incubation, MAS0141aa was tested for inhibition of lectin pathway of the complement system by cynomolgus monkey C3c ELISA assay. As shown in FIG. 4, MAS0141aa significantly inhibited cynomolgus monkey C3c deposition after the incubation. There was no difference in neutralizing activity of MAS0141aa between pre and post-incubation.

Figure 5:
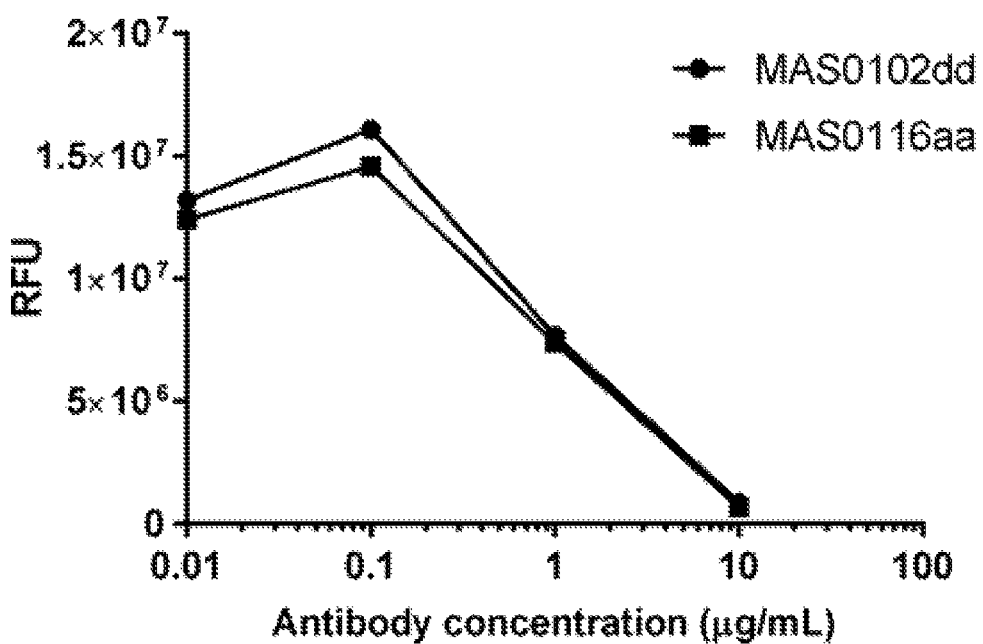
FIG. 5 illustrates the inhibitory effect of anti-MASP-1 monoclonal antibodies on MASP-1 enzymatic activity with a fluorogenic peptide.

4.4 Inhibition of Enzymatic Activity of the Active Form of MASP-1 by Anti-MASP-1 mAbs Anti-MASP-1 mAbs (MAS0102dd and MAS0116aa) were tested for inhibition of recombinant human MASP-1 (CCP1-CCP2-SP) (SEQ ID NO: 15) by a peptide cleavage assay. Boc-VPR-AMC was used as an artificial fluorogenic substrate of MASP-1. Twenty-five microliters of recombinant active-form human MASP-1 (CCP1-CCP2-SP) (0.4 micro g/mL) was mixed with 25 micro L of diluted mAb and 50 micro L of Boc-VPR-AMC (0.2 mM, R&D system) as a substrate in a 96-well plate (MS-8596K, Sumitomo Bakelite). The plate was incubated for 30 min at 37 degrees C., and relative fluorescence units (RFU) were measured at an excitation wavelength of 380 nm and an emission wavelength of 460 nm. FIG. 5 shows that both MAS0102dd and MAS0116aa are capable of neutralizing the active form of human MASP-1.

Example 5

In Vivo Study of Anti-MASP1 mAb in C57BL Mice

In vivo neutralization of the lectin pathway was assessed after the administration of anti-MASP-1 mAb in C57BL mice (In Vivos, Singapore).

MAS0154dd01-mF18 was generated from the chimeric mAb MAS0154dd obtained in Example 3. The heavy chain variable region of MAS0154dd01-mF18 was the same as MAS0154dd. The light chain variable region of MAS0154dd01-mF18 (SEQ ID NO: 68) was generated by substituting Cys at position 80 in the light chain variable region of MAS0154dd (SEQ ID NO: 29) with Ser to remove Cys residue in framework 3 of the light chain variable region. The heavy and light chain constant regions of MAS0154dd were changed to mF18 (SEQ ID NO: 69) and mk1 (SEQ ID NO: 70), respectively.

Figure 6:
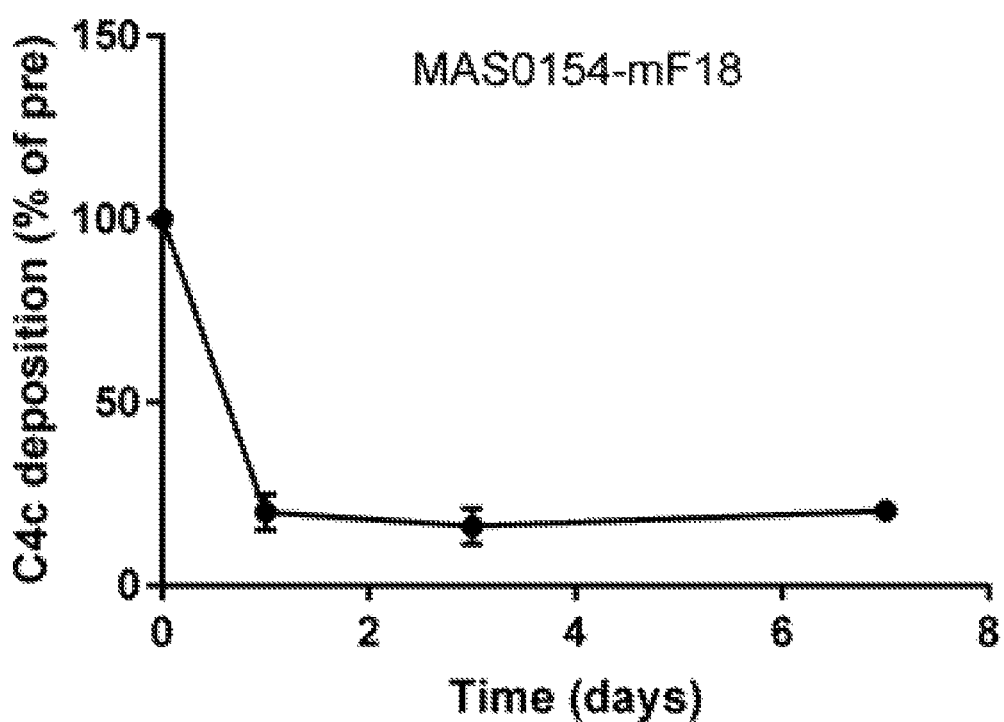
FIG. 6 illustrates the in vivo inhibitory effect of anti-MASP-1 monoclonal antibody MAS0154-mF18 on the lectin pathway in mice.

MAS0154-mF18 (3 mg/ml) was administered once at a dose of 10 ml/kg into the caudal vein. Blood was collected 1 day, 3 days, and 7 days after administration. The collected blood was immediately centrifuged at 14,000 rpm and 4 degrees C. for 10 min to separate the plasma. The separated plasma was stored in a refrigerator at −80 degrees C. before assay. To measure C4 activation, a 96-well plate was coated with mannan (20 micro g/mL) at 4 degrees C. overnight followed by blocking with TBS blocking buffer (Block Ace Powder, DS Pharma Biomedical) containing 0.5% bovine serum albumin (Roche Diagnostics) for 2 hours at 37 degrees C. Fifty microliters of mouse plasma samples (0.5%) were transferred into the mannan-coated plates and incubated for 1 hour at 37 degrees C. After washing the plates, C4c deposition was detected using a rabbit anti-C4c antibody (Dako) biotinylated in-house, followed by Streptavidin-HRP and development with ABTS (KPL). As shown in FIG. 6, anti-MASP-1 mab MAS0154-mF18 inhibited the lectin pathway activity in mice.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCE LISTING

C1-A1707Psq.txt

The invention claimed is:

1. An anti-MASP-1 antibody which specifically binds to MASP-1 wherein the antibody is selected from the group consisting of:
   (a) an antibody comprising the HVR-H1 sequence of SEQ ID NO: 32, the HVR-H2 sequence of SEQ ID NO: 33, the HVR-H3 sequence of SEQ ID NO: 34, the HVR-L1 sequence of SEQ ID NO: 35, the HVR-L2 sequence of SEQ ID NO: 36, and the HVR-L3 sequence of SEQ ID NO: 37;
   (b) an antibody comprising the HVR-H1 sequence of SEQ ID NO: 38, the HVR-H2 sequence of SEQ ID NO: 39, the HVR-H3 sequence of SEQ ID NO: 40, the HVR-L1 sequence of SEQ ID NO: 41, the HVR-L2 sequence of SEQ ID NO: 42, and the HVR-L3 sequence of SEQ ID NO: 43;
   (c) an antibody comprising the HVR-H1 sequence of SEQ ID NO: 44, the HVR-H2 sequence of SEQ ID NO: 45, the HVR-H3 sequence of SEQ ID NO: 46, the HVR-L1 sequence of SEQ ID NO: 47, the HVR-L2 sequence of SEQ ID NO: 48, and the HVR-L3 sequence of SEQ ID NO: 49;
   (d) an antibody comprising the HVR-H1 sequence of SEQ ID NO: 50, the HVR-H2 sequence of SEQ ID NO: 51, the HVR-H3 sequence of SEQ ID NO: 52, the HVR-L1 sequence of SEQ ID NO: 53, the HVR-L2 sequence of SEQ ID NO: 54, and the HVR-L3 sequence of SEQ ID NO: 55;
   (e) an antibody comprising the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 59, the HVR-L2 sequence of SEQ ID NO: 60, and the HVR-L3 sequence of SEQ ID NO: 61; and
   (f) an antibody comprising the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 65, the HVR-L2 sequence of SEQ ID NO: 66, and the HVR-L3 sequence of SEQ ID NO: 67.

2. The anti-MASP-1 antibody according to claim 1, wherein the antibody comprises the HVR-H1 sequence of SEQ ID NO: 32, the HVR-H2 sequence of SEQ ID NO: 33, the HVR-H3 sequence of SEQ ID NO: 34, the HVR-L1 sequence of SEQ ID NO: 35, the HVR-L2 sequence of SEQ ID NO: 36, and the HVR-L3 sequence of SEQ ID NO: 37.

3. The anti-MASP-1 antibody according to claim 1, wherein the antibody comprises the HVR-H1 sequence of SEQ ID NO: 38, the HVR-H2 sequence of SEQ ID NO: 39, the HVR-H3 sequence of SEQ ID NO: 40, the HVR-L1 sequence of SEQ ID NO: 41, the HVR-L2 sequence of SEQ ID NO: 42, and the HVR-L3 sequence of SEQ ID NO: 43.

4. The anti-MASP-1 antibody according to claim 1, wherein the antibody comprises the HVR-H1 sequence of SEQ ID NO: 44, the HVR-H2 sequence of SEQ ID NO: 45, the HVR-H3 sequence of SEQ ID NO: 46, the HVR-L1 sequence of SEQ ID NO: 47, the HVR-L2 sequence of SEQ ID NO: 48, and the HVR-L3 sequence of SEQ ID NO: 49.

5. The anti-MASP-1 antibody according to claim 1, wherein the antibody comprises the HVR-H1 sequence of SEQ ID NO: 50, the HVR-H2 sequence of SEQ ID NO: 51, the HVR-H3 sequence of SEQ ID NO: 52, the HVR-L1 sequence of SEQ ID NO: 53, the HVR-L2 sequence of SEQ ID NO: 54, and the HVR-L3 sequence of SEQ ID NO: 55.

6. The anti-MASP-1 antibody according to claim 1, wherein the antibody comprises the HVR-H1 sequence of SEQ ID NO: 56, the HVR-H2 sequence of SEQ ID NO: 57, the HVR-H3 sequence of SEQ ID NO: 58, the HVR-L1 sequence of SEQ ID NO: 59, the HVR-L2 sequence of SEQ ID NO: 60, and the HVR-L3 sequence of SEQ ID NO: 61.

7. The anti-MASP-1 antibody according to claim 1, wherein the antibody comprises the HVR-H1 sequence of SEQ ID NO: 62, the HVR-H2 sequence of SEQ ID NO: 63, the HVR-H3 sequence of SEQ ID NO: 64, the HVR-L1 sequence of SEQ ID NO: 65, the HVR-L2 sequence of SEQ ID NO: 66, and the HVR-L3 sequence of SEQ ID NO: 67.

8. The anti-MASP-1 antibody according to claim 1, wherein the antibody inhibits MASP-1 activity.

9. The anti-MASP-1 antibody according to claim 8, wherein the antibody does not inhibit MASP-3 activity.

10. The anti-MASP-1 antibody according to claim 9, wherein the MASP-1 activity is MASP-1 mediated complement lectin-pathway activation and the MASP-3 activity is MASP-3 mediated complement lectin-pathway activation.

11. The anti-MASP-1 antibody according to claim 1, wherein the antibody is capable of binding to, and inhibiting activity of, human MASP-1, cynomolgus monkey MASP-1, and/or mouse MASP-1.

12. A pharmaceutical composition comprising the antibody according to claim 1 and a pharmaceutically acceptable carrier.

13. The anti-MASP-1 antibody according to claim 1, that comprises a human IgG1, IgG2, IgG3, or IgG4 Fc sequence.

14. The anti-MASP-1 antibody according to claim 1, that comprises a modified human IgG Fc sequence.

15. The anti-MASP-1 antibody according to claim 1, that comprises a modified human IgG Fc sequence that lacks Fc gamma R binding but retains FcRn binding.

16. The anti-MASP-1 antibody according to claim 1, that comprises a modified human IgG heavy chain constant region having the sequence of SEQ ID NO:18.

\* \* \* \* \*